(12) United States Patent
McGrail et al.

(10) Patent No.: US 6,902,888 B1
(45) Date of Patent: Jun. 7, 2005

(54) DIABETES GENE

(75) Inventors: Maura McGrail, Salt Lake City, UT (US); Deanna L. Russell, Salt Lake City, UT (US); Donna M. Shattuck, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 0 days.

(21) Appl. No.: 09/573,425

(22) Filed: May 16, 2000

Related U.S. Application Data

(60) Provisional application No. 60/174,700, filed on Jan. 6, 2000, and provisional application No. 60/135,423, filed on May 21, 1999.

(51) Int. Cl.$^7$ ............... C12Q 1/68; C12P 19/34; C07H 21/02; C07H 21/04

(52) U.S. Cl. ............... 435/6; 435/91.1; 536/23.1; 536/23.5; 536/24.31

(58) Field of Search ............... 435/6, 91.1; 536/23.1, 536/24.31, 23.5

(56) References Cited

U.S. PATENT DOCUMENTS

| | | |
|---|---|---|
| 5,589,584 A | 12/1996 | Lalouel et al. |
| 5,916,907 A | 6/1999 | Bird |

FOREIGN PATENT DOCUMENTS

| | | |
|---|---|---|
| WO | 9519568 | 7/1995 |
| WO | 9718312 | 5/1997 |
| WO | 9728684 | 8/1997 |
| WO | 9858952 | 12/1998 |

OTHER PUBLICATIONS

Rogus et al. Hypertension, Feb. 1998, vol. 31, No. 2, pp. 627–631.*
Accession No. AA798473, Marra et al. 1996 Est Project, Wash U.*
Yanai, K. et al. (1999). *J. Biol. Chem.* 274:(49):34605–34612.
O'Byrne, S. et al. (1998). "Genetics of Hypertension," *Drugs 1998*, Aug. 56(2), pp. 203–214.
Lindner, T. et al. (1997). *J. Clin. Invest.* 100 (6):1400–1405.
Yamagata, K. et al. (1996). *Nature* 384:458–460.
Ohno, T. et al. (1996). "Association Analysis of the Polymorphisms of Angiotensin–Converting Enzyme and Angiotensinogen Genes with Diabetic Nephropathy in Japanese Non–Insulin–Dependent Diabetics," Gunma University School of Medicine, Gunma, Japan, paper accepted Aug. 27, 1995, pp. 218–222.
Hixson, J. et al. (1995), *Hum. Genet.* 96:110–112.

* cited by examiner

*Primary Examiner*—Sean McGarry
*Assistant Examiner*—Jane Zara
(74) *Attorney, Agent, or Firm*—Rothwell, Figg, Ernst & Manbeck

(57) ABSTRACT

The present invention relates generally to the field of human genetics. Specifically, the present invention relates to methods and materials used to isolate and detect human diabetes mellitus predisposing gene, specifically the angiotensinogen (AGT) gene, some mutant alleles of which cause susceptibility to insulin-dependent diabetes mellitus (IDDM). More specifically, the invention relates to gernline mutations in the AGT gene and their use in the diagnosis of predisposition to diabetes. The invention also relates to the prophylaxis and/or therapy of diabetes associated with a mutation in the AGT gene. The invention further relates to the screening of drugs for diabetes therapy. Finally, the invention relates to the screening of the AGT gene for mutations, which are useful for diagnosing the predisposition to diabetes.

7 Claims, 3 Drawing Sheets

SEQUENCE LISTING

```
<160> NUMBER OF SEQ ID NOS:  68

<210> SEQ ID NO 1
<211> LENGTH: 5308
<212> TYPE: DNA
<213> ORGANISM: Homo sapiens
<220> FEATURE:
<221> NAME/KEY: misc_feature
<222> LOCATION: (3012)..(3047)
<223> OTHER INFORMATION: exon 1 of AGT gene

<400> SEQUENCE: 1
gccccagcca cttgacccaa cctggagctc acaaaacccc gtgttgtata aaagtaaggt      60
ttaagggtct agggctgtgt caaagtggct ggggcaaagc tacaaattaa caacatctca     120
gcaaagcaat tgtttaaagt acagctcttt ttcaaaatgg agtctcttat gtcttccctt     180
tctatataga cacagtaaca gtctgatctc tctttttttt ccctacatat cccaatagca     240
cctgcctgac taatacatca tgctctgctg actccatatg tggctggttt cctggatccg     300
attctgactg atggtatctg ttctcacgct gctaataaag acataccaga gactgggtaa     360
```

-continued

```
tttataaaga aaaagaggtt taatggactt atgtgttcca cgtggctggg gaggcctcac    420
aatcatggtg gaaggtgaag gaggagcaaa agcacatctt acatggtggc tggcaaaaga    480
gagaaagcat gttcagggga actcccsttt ataaaaccat cagatctcat gagacttatg    540
cactatcaca agaacagcac cagaaagatc caccctcatg attcaattac ctcccactgg    600
gtccctcccg tgacacatgg gaattatggg agctacaatt ggagatttgg gtggggacac    660
agccaaacca tatcagatgg cttatttggt ttctatgtag aacctctgct tttcattcaa    720
cagtcttcat ttagccacag ataagctctg tccctaactt ccgctgatgg aatgtacaca    780
taagaaactt ccactgatgg aatgaacaca gaaggtgcct actgggaaga aaactggcct    840
gaatctgagc tgggtcaaat gtctgcagtc agtttgaatg gctgctcctt atgggaataa    900
tttacattct caataaaatt ctctagcaat tttctgatta ttttaatga gctttaaagc    960
cttacgtaga agatccccca gctgatagtc agccttgggc atggattaag ggcttttaac   1020
caatcttgca acaagtttaa gcagatattc tttattgggt ccaatctaac caaaattatt   1080
ttcttatgtt ctccccagta acgtgtcatt attaagagaa gtttggcttg cttagaggcc   1140
aaatttagag ggtcctgaaa ttttattttc ttttacacca ctttccagca tgttacctga   1200
tcagttgttt attatctttg ctgttgaatg gagtgatcat tccaagggcc cgaggcagga   1260
ggcccaggca cagtggaaac tctcccaaag accaggatct ttgttttgtt ccctgacata   1320
tgctgagcac caggaatagt gaatgaatga aacaaattgt gaggctttaa agagccgaaa   1380
tatttaaaca ctgggcacaa ggttgttgct taatcagtgc tagatcctta cctccccctt   1440
gtgtccaggt cgacttgtta ctgcagttaa accacttgct gatcctcaaa caactagtta   1500
gtggcacagc caggcctagg accccagtct ctactgttcc aactaaccca ttcgcaggca   1560
ggagcacttt gaatggtctc ttatttaaa aaaattaaat taaaattgtc tatttattta   1620
gagacagagt cttactctgt agcccaggct cgagtgcagt ggtgcaatca tagctcactg   1680
taacctccat ctcctggcct caaaaagtgt ttgaattaca gatgcgaggc actgtacctg   1740
gcccgaatgt tctgttcaga caaagccacc tctaagtcgc tgtggggccc cagacaagtg   1800
atttttgagg agtccctatc tataggaaca aagtaattaa aaaaatgtat ttcagaattt   1860
acaggcccat gtgagatatg attttttttaa atgaagattt agagtaatgg gtaaaaaaga   1920
ggtatttgtg tgtttgttga ttgttcagtc agtgaatgta cagcttctgc ctcatatcca   1980
ggcaccatct cttcctgctc tttgttgtta aatgttccat tcctgggtaa tttcatgtct   2040
gccatcgtgg atatgccgtg gctccttgaa cctgcttgtg ttgaagcagg atcttccttc   2100
ctgtcccttc agtgccctaa taccatgtat ttaaggctgg acacatcacc actcccaacc   2160
tgcctcaccc actgcgtcac ttgtgatcac tggcttctgg cgactctcac caaggtctct   2220
gtcatgccct gttataacga ctacaaaagc aagtcttacc tataggaaaa taagaattat   2280
aacccttta ctggtcatgt gaaacttacc atttgcaatt tgtacagcat aaacacagaa   2340
cagcacatct ttcaatgcct gcatcctgaa ggcattttgt ttgtgtcttt caatctggct   2400
gtgctattgt tggtgtttaa cagtctcccc agctacactg gaaacttcca gaaggcactt   2460
ttcacttgct tgtgtgtttt ccccagtgtc tattagaggc cttgcacag gtaggctct   2520
ttggagcagc tgaaggtcac acatcccatg agcgggcagc agggtcagaa gtggcccccg   2580
tgttgcctaa gcaagactct cccctgccct ctgccctctg cacctccggc ctgcatgtcc   2640
ctgtggcctt tgggggtac atctcccggg gctgggtcag aaggcctggg tggttggcct   2700
caggctgtca cacacctagg gagatgctcc cgtttctggg aaccttggcc ccgactcctg   2760
```

-continued

```
caaacttcgg taaatgtgta actcgaccct gcaccggctc actctgttca gcagtgaaac    2820
tctgcatcga tcactaagac ttcctggaag aggtcccagc gtgagtgtcg cttctggcat    2880
ctgtccttct ggccagcctg tggtctggcc aagtgatgta accctcctct ccagcctgtg    2940
cacaggcagc ctgggaacag ctccatcccc acccctcagc tataaatagg gcatcgtgac    3000
ccggccaggg aagaagctg ccgttgttct gggtactaca gcagaaggta agccgggggc     3060
cccctcagct ccttctcggc cttgtctctc tcagatgtaa ctgagctgtg ggctaggagg    3120
aaaaggcccg ggaggaggca cggtgatgac tgaaaaacct ctcccctctc ataagaccag    3180
tcatccggac gcgggctttc ccccactcgg tgcccacctg gggtcttaca ggaggagctg    3240
ctcctcctca gcataggac aagatggtca ggtcttcctg ttccgctgag aaaagttagg     3300
gtcctcagga acggagcaga ctggtacagg aacagagtca tcatggccaa gagtccaccg    3360
ggtcctcttg ccatcaggag aatagcagg gcttgtgcag gaattggggc tggagggaag     3420
ggccgggctc ggtcagtctc cagctgggat ccccagagtg gtcaccctac ccctccctcg    3480
agacagactg cctgactgtg tgtcatcagg ctggtcaccg tctccctgaa cctcgatttg    3540
ctcacctata aatggaact aataacgatg cctgggctcc ctgtctcagg ggctctggta     3600
tagctgaaga gaactaatat aacatgaaag tgctttctaa gctttgggat aagctaaaag    3660
gcagattcca attttattcg agggcagcgt agattggtgc ttcagctcgt ggatgacaga    3720 gtcaggggc ctggttctga gtcctagttc tgtctcttcc cagctgtgtg acgttgaaca     3780
agccactgga cctctctgtt cctctgcaaa acagcatgaa ccaattcatt aactacttct    3840
ccaggatgca gtaggtccca gggactatcc taggaatgtg ggctgtatta gtaaacacaa    3900
cagcgggaac cctgttccgg ggctcacatt cacatcagag caaacagaca aagacgctgg    3960
acagaataag tgcataacta catggtacag agggttataa ggagggaaaa ggggagctgg    4020
atgagagagt tgagagtgcc cggtgtggtg gggaaagctg cagggtgaaa tactgcatca    4080
gggaaacctc agggaaggtg aggactatgg tgaggtcaga ggggttgata tgagaacagt    4140
gccctgcaaa tggcaggcac cacaggagca tgagccgtca tcttcacctt tagcattcag    4200
cccgggagaa gtagggagac atagaagggg caggtgctgg ccaagaggca ggggcaggag    4260
aggagaaggc ggaggggcac tcagggcgag ggtgtcaggc ccgccacccc agagcaccat    4320
tactcccagg acgcggctgc gtgcagacct ggaaccagcc tagggagcag ccgcagatca    4380
caactgagaa caaacgacag tctctgcctc aaaaatggcc catggaattg cgtctctgga    4440
gacgctgcct gagcaggagc agcacagtga gcgggctgca tcgaccagcg ccatccaaac    4500
cccgaacagt tggcgcttgt caggcaggac ttcccagcag tcggttccca caggtttccc    4560
ctgttgacct gatttgatgt gactgtctag attaggtgtg aactggtggc ttaggcttct    4620
ctgcacagaa aggcctgcaa gcagcagaga gagttttctg ttccattttt ccatgtcatg    4680
tggctcttcc tgagaacagc ggatggagtc aaatgcatgg ggagtggggt gagatggtag    4740
ctgaggtcag aatttggcat ttgaatgact gaagcagaac aaaacacacc aggtacttca    4800
gcagctgcac cgtgttgagg gcaggtgctg gttacgggtc tgggtgaggg aagccagctg    4860
ccaatgtaag aagaatgact gggtatgctt agatgaagca gaaaaatcta ggcatcaagg    4920
tggccttgag tcagtgatga cacgctacag ctccaaggaa gcctggccta gccctggggg    4980
gacagaaaag gccaagaagt gacgatattg cagtacaccc cctccacaa gaaatgagtg     5040 agatgtggta caaaatgtta gaattgaatg aatcaataga ataaacgttc atcccttcaa    5100
```

-continued

| | |
|---|---|
| tcaagaagag tcagatgaaa tgaattagca gggccagccc aagaacctct tctggggtc | 5160 |
| tcagggtagc tttcatttgt agcagctgag gcggaaccag ctgtaaggcc tttgagagaa | 5220 |
| cgtggtgctg gacccgtgtc tagggcaggg gttctaaacc ctgcttacat atcagagtca | 5280 |
| cctgagaatt ttctattttt ttttttt | 5308 |

<210> SEQ ID NO 2
<211> LENGTH: 1159
<212> TYPE: DNA
<213> ORGANISM: Homo sapiens
<220> FEATURE:
<221> NAME/KEY: misc_feature
<222> LOCATION: (151)..(1009)
<223> OTHER INFORMATION: exon 2 of AGT gene

<400> SEQUENCE: 2

| | |
|---|---|
| aatccatttc ttcttttttt tgtagacatg aatggattta ttctgggcta aatggtgaca | 60 |
| gggaatattg agacaatgaa agatctggtt agatggcact taaaggtcag ttaataacca | 120 |
| cctttcaccc tttgcaaaat gatatttcag ggtatgcgga agcgagcacc ccagtctgag | 180 |
| atggctcctg ccggtgtgag cctgaggcc accatcctct gcctcctggc ctgggctggc | 240 |
| ctggctgcag gtgaccgggt gtacatacac cccttccacc tcgtcatcca caatgagagt | 300 |
| acctgtgagc agctggcaaa ggccaatgcc gggaagccca agacccccac cttcatacct | 360 |
| gctccaattc aggccaagac atcccctgtg gatgaaaagg ccctacagga ccagctggtg | 420 |
| ctagtcgctg caaaacttga caccgaagac aagttgaagg ccgcaatggt cgggatgctg | 480 |
| gccaacttct tgggcttccg tatatatggc atgcacagtg agctatgggg cgtggtccat | 540 |
| ggggccaccg tcctctcccc aacggctgtc tttggcaccc tggcctctct ctatctggga | 600 |
| gccttggacc acacagctga caggctacag gcaatcctgg gtgttccttg gaaggacaag | 660 |
| aactgcacct cccggctgga tgcgcacaag gtcctgtctg ccctgcaggc tgtacagggc | 720 |
| ctgctagtgg cccagggcag ggctgatagc caggcccagc tgctgctgtc cacggtggtg | 780 |
| ggcgtgttca cagccccagg cctgcacctg aagcagccgt ttgtgcaggg cctggctctc | 840 |
| tatacccctg tggtcctccc acgctctctg gacttcacag aactggatgt tgctgctgag | 900 |
| aagattgaca ggttcatgca ggctgtgaca ggatggaaga ctggctgctc cctgacggga | 960 |
| gccagtgtgg acagcaccct ggctttcaac acctacgtcc acttccaagg taaggcaaac | 1020 |
| ctctctgctg gctctggccc taggacttag tatccaatgt gtagctgaga tcagccagtc | 1080 |
| aggccttgga gatgggcagg gggcagccct gcggacatac ctggtgacca cccttgagaa | 1140 |
| gtggggaagt ggcctctcc | 1159 |

<210> SEQ ID NO 3
<211> LENGTH: 568
<212> TYPE: DNA
<213> ORGANISM: Homo sapiens
<220> FEATURE:
<221> NAME/KEY: misc_feature
<222> LOCATION: (151)..(418)
<223> OTHER INFORMATION: exon 3 of AGT gene

<400> SEQUENCE: 3

| | |
|---|---|
| ccaggagaat gcagagtggc ctgggggggg ccaaggaagg aggctgaggc agggcgaggg | 60 |
| gcaggatctg ggcctttggt gtctgccagc cctcattcct gcccctgtct tgggtgactc | 120 |
| ttccctcccc gtcctgtc tggatttcag ggaagatgaa gggcttctcc ctgctggccg | 180 |
| agcccccagga gttctgggtg gacaacagca cctcagtgtc tgttcccatg ctctctggca | 240 |

```
tgggcacctt ccagcactgg agtgacatcc aggacaactt ctcggtgact caagtgccct    300
tcactgagag cgcctgcctg ctgctgatcc agcctcacta tgcctctgac ctggacaagg    360
tggagggtct cactttccag caaaactccc tcaactggat gaagaaactg tctcccggt     420 aggagcctcc cggtctcccc tggaatgtgg gagccacact gtcctgccca ggctggggc     480 ggggtgggga gtagacacac ctgagctgag ccttgggtgc agagcagggc agggccgcgg    540
tggcacgggg ctgggcaggc ggcctgtg                                       568

<210> SEQ ID NO 4
<211> LENGTH: 445
<212> TYPE: DNA
<213> ORGANISM: Homo sapiens
<220> FEATURE:
<221> NAME/KEY: misc_feature
<222> LOCATION: (151)..(295)
<223> OTHER INFORMATION: exon 4 of AGT gene

<400> SEQUENCE: 4 cccaagggg aggatgactt agttgggtga tggggggagc aaacatccct gtcgtcaggg      60
ttgggtgcaa ggagcataag cctgcctggc ctctgggaga gccctcactg tgtggcctgg   120
agccttccta actgtgcatc atctccccag gaccatccac ctgaccatgc ccaactggt    180 gctgcaagga tcttatgacc tgcaggacct gctcgcccag gctgagctgc ccgccattct   240
gcacaccgag ctgaacctgc aaaaattgag caatgaccgc atcagggtgg gggaggtatg   300
tgtgagcctg tgtctgtgcc tgacctgggt tccaagtgtg cacagggtgg gaggcatgga   360
tgtaagggac acagaggagg ctatgggtgg ggccagcagg gcaagaggga gcggagagta   420
gggccaaagg tgggagagaa gtagc                                         445

<210> SEQ ID NO 5
<211> LENGTH: 1091
<212> TYPE: DNA
<213> ORGANISM: Homo sapiens
<220> FEATURE:
<221> NAME/KEY: misc_feature
<222> LOCATION: (151)..(941)
<223> OTHER INFORMATION: exon 5 of AGT gene

<400> SEQUENCE: 5
actgtgcatc ctcctggcag gctggaaaat gtcccctcc aggacagtgc acagcacaga     60
ggtcctgagc ccaccccggc cctctagccc tcagcaccct gggtcaccca gtgcgccctc   120
agaatgatcc tgatgtctgc tgctttgcag gtgctgaaca gcattttttt tgagcttgaa   180
gcggatgaga gagagcccac agagtctacc caacagctta acaagcctga ggtcttggag   240 gtgacccctga accgcccatt cctgtttgct gtgtatgatc aaagcgccac tgccctgcac   300
ttcctgggcc gcgtggccaa cccgctgagc acagcatgag gccagggccc cagaacacag   360
tgcctggcaa ggcctctgcc cctggccttt gaggcaaagg ccagcagcag ataacaaccc   420
cggacaaatc agcgatgtgt caccccagt ctcccacctt ttcttctaat gagtcgactt    480
tgagctggaa agcagccgtt tctccttggt ctaagtgtgc tgcatggagt gagcagtaga   540
agcctgcagc ggcacaaatg cacctcccag tttgctgggt ttattttaga gaatgggggt   600
ggggaggcaa gaaccagtgt ttagcgcggg actactgttc caaaaagaat ccaaccgac    660 cagcttgttt gtgaaacaaa aaagtgttcc cttttcaagt tgagaacaaa aattgggttt   720
taaaattaaa gtatacattt ttgcattgcc ttcggtttgt atttagtgtc ttgaatgtaa   780
```

-continued

| | |
|---|---|
| gaacatgacc tccgtgtagt gtctgtaata ccttagtttt ttccacagat gcttgtgatt | 840 |
| tttgaacaat acgtgaaaga tgcaagcacc tgaatttctg tttgaatgcg gaaccatagc | 900 |
| tggttatttc tcccttgtgt tagtaataaa cgtcttgcca caataagcct ccaaaaattt | 960 |
| tatctttcat ttagcagcca aacagatgta tacaattcag cagatagact gtgcaaacga | 1020 |
| aagtgctttc ctggactttg gatggaattt ccatgggagg tctgagccag tacttagcag | 1080 |
| tcctttgaag t | 1091 |

<210> SEQ ID NO 6
<211> LENGTH: 2099
<212> TYPE: DNA
<213> ORGANISM: Homo sapiens
<220> FEATURE:
<221> NAME/KEY: CDS
<222> LOCATION: (40)..(1494)
<221> NAME/KEY: sig_peptide
<222> LOCATION: (40)..(138)

<400> SEQUENCE: 6

| | |
|---|---|
| aagaagctgc cgttgttctg ggtactacag cagaagggt atg cgg aag cga gca<br>                                                           Met Arg Lys Arg Ala<br>                                                          1               5 | 54 |
| ccc cag tct gag atg gct cct gcc ggt gtg agc ctg agg gcc acc atc<br>Pro Gln Ser Glu Met Ala Pro Ala Gly Val Ser Leu Arg Ala Thr Ile<br>          10                   15                    20 | 102 |
| ctc tgc ctc ctg gcc tgg gct ggc ctg gct gca ggt gac cgg gtg tac<br>Leu Cys Leu Leu Ala Trp Ala Gly Leu Ala Ala Gly Asp Arg Val Tyr<br>              25                    30                    35 | 150 |
| ata cac ccc ttc cac ctc gtc atc cac aat gag agt acc tgt gag cag<br>Ile His Pro Phe His Leu Val Ile His Asn Glu Ser Thr Cys Glu Gln<br>          40                   45                    50 | 198 |
| ctg gca aag gcc aat gcc ggg aag ccc aaa gac ccc acc ttc ata cct<br>Leu Ala Lys Ala Asn Ala Gly Lys Pro Lys Asp Pro Thr Phe Ile Pro<br>55                  60                    65 | 246 |
| gct cca att cag gcc aag aca tcc cct gtg gat gaa aag gcc cta cag<br>Ala Pro Ile Gln Ala Lys Thr Ser Pro Val Asp Glu Lys Ala Leu Gln<br>70                  75                    80                    85 | 294 |
| gac cag ctg gtg cta gtc gct gca aaa ctt gac acc gaa gac aag ttg<br>Asp Gln Leu Val Leu Val Ala Ala Lys Leu Asp Thr Glu Asp Lys Leu<br>                  90                    95                   100 | 342 |
| aag gcc gca atg gtc ggg atg ctg gcc aac ttc ttg ggc ttc cgt ata<br>Lys Ala Ala Met Val Gly Met Leu Ala Asn Phe Leu Gly Phe Arg Ile<br>              105                   110                   115 | 390 |
| tat ggc atg cac agt gag cta tgg ggc gtg gtc cat ggg gcc acc gtc<br>Tyr Gly Met His Ser Glu Leu Trp Gly Val Val His Gly Ala Thr Val<br>          120                   125                   130 | 438 |
| ctc tcc cca acg gct gtc ttt ggc acc ctg gcc tct ctc tat ctg gga<br>Leu Ser Pro Thr Ala Val Phe Gly Thr Leu Ala Ser Leu Tyr Leu Gly<br>135                 140                   145 | 486 |
| gcc ttg gac cac aca gct gac agg cta cag gca atc ctg ggt gtt cct<br>Ala Leu Asp His Thr Ala Asp Arg Leu Gln Ala Ile Leu Gly Val Pro<br>150                 155                   160                   165 | 534 |
| tgg aag gac aag aac tgc acc tcc cgg ctg gat gcg cac aag gtc ctg<br>Trp Lys Asp Lys Asn Cys Thr Ser Arg Leu Asp Ala His Lys Val Leu<br>              170                   175                   180 | 582 |
| tct gcc ctg cag gct gta cag ggc ctg cta gtg gcc cag ggc agg gct<br>Ser Ala Leu Gln Ala Val Gln Gly Leu Leu Val Ala Gln Gly Arg Ala<br>              185                   190                   195 | 630 |
| gat agc cag gcc cag ctg ctg ctg tcc acg gtg gtg ggc gtg ttc aca<br>Asp Ser Gln Ala Gln Leu Leu Leu Ser Thr Val Val Gly Val Phe Thr | 678 |

-continued

| | | | | | | | | | | | | | | | | |
|---|---|---|---|---|---|---|---|---|---|---|---|---|---|---|---|---|
| | | 200 | | | | | 205 | | | | | 210 | | | | |
| gcc | cca | ggc | ctg | cac | ctg | aag | cag | ccg | ttt | gtg | cag | ggc | ctg | gct | ctc | 726 |
| Ala | Pro | Gly | Leu | His | Leu | Lys | Gln | Pro | Phe | Val | Gln | Gly | Leu | Ala | Leu | |
| | 215 | | | | | 220 | | | | | 225 | | | | | |
| tat | acc | cct | gtg | gtc | ctc | cca | cgc | tct | ctg | gac | ttc | aca | gaa | ctg | gat | 774 |
| Tyr | Thr | Pro | Val | Val | Leu | Pro | Arg | Ser | Leu | Asp | Phe | Thr | Glu | Leu | Asp | |
| 230 | | | | | 235 | | | | | 240 | | | | | 245 | |
| gtt | gct | gct | gag | aag | att | gac | agg | ttc | atg | cag | gct | gtg | aca | gga | tgg | 822 |
| Val | Ala | Ala | Glu | Lys | Ile | Asp | Arg | Phe | Met | Gln | Ala | Val | Thr | Gly | Trp | |
| | | | | 250 | | | | | 255 | | | | | 260 | | |
| aag | act | ggc | tgc | tcc | ctg | acg | gga | gcc | agt | gtg | gac | agc | acc | ctg | gct | 870 |
| Lys | Thr | Gly | Cys | Ser | Leu | Thr | Gly | Ala | Ser | Val | Asp | Ser | Thr | Leu | Ala | |
| | | 265 | | | | | 270 | | | | | 275 | | | | |
| ttc | aac | acc | tac | gtc | cac | ttc | caa | ggg | aag | atg | aag | ggc | ttc | tcc | ctg | 918 |
| Phe | Asn | Thr | Tyr | Val | His | Phe | Gln | Gly | Lys | Met | Lys | Gly | Phe | Ser | Leu | |
| | 280 | | | | | 285 | | | | | 290 | | | | | |
| ctg | gcc | gag | ccc | cag | gag | ttc | tgg | gtg | gac | aac | agc | acc | tca | gtg | tct | 966 |
| Leu | Ala | Glu | Pro | Gln | Glu | Phe | Trp | Val | Asp | Asn | Ser | Thr | Ser | Val | Ser | |
| 295 | | | | | 300 | | | | | 305 | | | | | | |
| gtt | ccc | atg | ctc | tct | ggc | atg | ggc | acc | ttc | cag | cac | tgg | agt | gac | atc | 1014 |
| Val | Pro | Met | Leu | Ser | Gly | Met | Gly | Thr | Phe | Gln | His | Trp | Ser | Asp | Ile | |
| 310 | | | | | 315 | | | | | 320 | | | | | 325 | |
| cag | gac | aac | ttc | tcg | gtg | act | caa | gtg | ccc | ttc | act | gag | agc | gcc | tgc | 1062 |
| Gln | Asp | Asn | Phe | Ser | Val | Thr | Gln | Val | Pro | Phe | Thr | Glu | Ser | Ala | Cys | |
| | | | 330 | | | | | 335 | | | | | 340 | | | |
| ctg | ctg | ctg | atc | cag | cct | cac | tat | gcc | tct | gac | ctg | gac | aag | gtg | gag | 1110 |
| Leu | Leu | Leu | Ile | Gln | Pro | His | Tyr | Ala | Ser | Asp | Leu | Asp | Lys | Val | Glu | |
| | | | 345 | | | | | 350 | | | | | 355 | | | |
| ggt | ctc | act | ttc | cag | caa | aac | tcc | ctc | aac | tgg | atg | aag | aaa | ctg | tct | 1158 |
| Gly | Leu | Thr | Phe | Gln | Gln | Asn | Ser | Leu | Asn | Trp | Met | Lys | Lys | Leu | Ser | |
| | | 360 | | | | | 365 | | | | | 370 | | | | |
| ccc | cgg | acc | atc | cac | ctg | acc | atg | ccc | caa | ctg | gtg | ctg | caa | gga | tct | 1206 |
| Pro | Arg | Thr | Ile | His | Leu | Thr | Met | Pro | Gln | Leu | Val | Leu | Gln | Gly | Ser | |
| | 375 | | | | | 380 | | | | | 385 | | | | | |
| tat | gac | ctg | cag | gac | ctg | ctc | gcc | cag | gct | gag | ctg | ccc | gcc | att | ctg | 1254 |
| Tyr | Asp | Leu | Gln | Asp | Leu | Leu | Ala | Gln | Ala | Glu | Leu | Pro | Ala | Ile | Leu | |
| 390 | | | | | 395 | | | | | 400 | | | | | 405 | |
| cac | acc | gag | ctg | aac | ctg | caa | aaa | ttg | agc | aat | gac | cgc | atc | agg | gtg | 1302 |
| His | Thr | Glu | Leu | Asn | Leu | Gln | Lys | Leu | Ser | Asn | Asp | Arg | Ile | Arg | Val | |
| | | | | 410 | | | | | 415 | | | | | 420 | | |
| ggg | gag | gtg | ctg | aac | agc | att | ttt | ttt | gag | ctt | gaa | gcg | gat | gag | aga | 1350 |
| Gly | Glu | Val | Leu | Asn | Ser | Ile | Phe | Phe | Glu | Leu | Glu | Ala | Asp | Glu | Arg | |
| | | | 425 | | | | | 430 | | | | | 435 | | | |
| gag | ccc | aca | gag | tct | acc | caa | cag | ctt | aac | aag | cct | gag | gtc | ttg | gag | 1398 |
| Glu | Pro | Thr | Glu | Ser | Thr | Gln | Gln | Leu | Asn | Lys | Pro | Glu | Val | Leu | Glu | |
| | | 440 | | | | | 445 | | | | | 450 | | | | |
| gtg | acc | ctg | aac | cgc | cca | ttc | ctg | ttt | gct | gtg | tat | gat | caa | agc | gcc | 1446 |
| Val | Thr | Leu | Asn | Arg | Pro | Phe | Leu | Phe | Ala | Val | Tyr | Asp | Gln | Ser | Ala | |
| | 455 | | | | | 460 | | | | | 465 | | | | | |
| act | gcc | ctg | cac | ttc | ctg | ggc | cgc | gtg | gcc | aac | ccg | ctg | agc | aca | gca | 1494 |
| Thr | Ala | Leu | His | Phe | Leu | Gly | Arg | Val | Ala | Asn | Pro | Leu | Ser | Thr | Ala | |
| 470 | | | | | 475 | | | | | 480 | | | | | 485 | | tgaggccagg gccccagaac acagtgcctg gcaaggcctc tgcccctggc ctttgaggca 1554 aaggccagca gcagataaca accccggaca aatcagcgat gtgtcacccc cagtctccca 1614 ccttttcttc taatgagtcg actttgagct ggaaagcagc cgtttctcct tggtctaagt 1674 gtgctgcatg gagtgagcag tagaagcctg cagcggcaca aatgcacctc ccagtttgct 1734 gggtttattt tagagaatgg gggtggggag gcaagaacca gtgtttagcg cgggactact 1794

-continued

```
gttccaaaaa gaattccaac cgaccagctt gtttgtgaaa caaaaaagtg ttccctttc    1854 aagttgagaa caaaaattgg gttttaaaat taaagtatac attttttgcat tgccttcggt   1914 ttgtatttag tgtcttgaat gtaagaacat gacctccgtg tagtgtctgt aatacctag    1974 tttttttccac agatgcttgt gatttttgaa caatacgtga aagatgcaag cacctgaatt   2034
tctgtttgaa tgcggaacca tagctggtta tttctcccctt gtgttagtaa taaacgtctt   2094
gccac                                                                2099
```

<210> SEQ ID NO 7
<211> LENGTH: 485
<212> TYPE: PRT
<213> ORGANISM: Homo sapiens

<400> SEQUENCE: 7

```
Met Arg Lys Arg Ala Pro Gln Ser Glu Met Ala Pro Ala Gly Val Ser
 1               5                  10                  15

Leu Arg Ala Thr Ile Leu Cys Leu Leu Ala Trp Ala Gly Leu Ala Ala
                20                  25                  30

Gly Asp Arg Val Tyr Ile His Pro Phe His Leu Val Ile His Asn Glu
            35                  40                  45

Ser Thr Cys Glu Gln Leu Ala Lys Ala Asn Ala Gly Lys Pro Lys Asp
        50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Lys Ala Ala Met Val Gly Met Leu Ala Asn Phe
            100                 105                 110

Leu Gly Phe Arg Ile Tyr Gly Met His Ser Glu Leu Trp Gly Val Val
        115                 120                 125

His Gly Ala Thr Val Leu Ser Pro Thr Ala Val Phe Gly Thr Leu Ala
    130                 135                 140

Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190

Ala Gln Gly Arg Ala Asp Ser Gln Ala Gln Leu Leu Leu Ser Thr Val
        195                 200                 205

Val Gly Val Phe Thr Ala Pro Gly Leu His Leu Lys Gln Pro Phe Val
    210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Thr Gly Ala Ser Val
            260                 265                 270

Asp Ser Thr Leu Ala Phe Asn Thr Tyr Val His Phe Gln Gly Lys Met
        275                 280                 285

Lys Gly Phe Ser Leu Leu Ala Glu Pro Gln Glu Phe Trp Val Asp Asn
    290                 295                 300

Ser Thr Ser Val Ser Val Pro Met Leu Ser Gly Met Gly Thr Phe Gln
```

```
                 305                 310                 315                 320
    His Trp Ser Asp Ile Gln Asp Asn Phe Ser Val Thr Gln Val Pro Phe
                    325                 330                 335

Thr Glu Ser Ala Cys Leu Leu Leu Ile Gln Pro His Tyr Ala Ser Asp
                    340                 345                 350

Leu Asp Lys Val Glu Gly Leu Thr Phe Gln Gln Asn Ser Leu Asn Trp
                    355                 360                 365

Met Lys Lys Leu Ser Pro Arg Thr Ile His Leu Thr Met Pro Gln Leu
            370                 375                 380

Val Leu Gln Gly Ser Tyr Asp Leu Gln Asp Leu Ala Gln Ala Glu
    385                 390                 395                 400

Leu Pro Ala Ile Leu His Thr Glu Leu Asn Leu Gln Lys Leu Ser Asn
                    405                 410                 415

Asp Arg Ile Arg Val Gly Glu Val Leu Asn Ser Ile Phe Phe Glu Leu
                    420                 425                 430

Glu Ala Asp Glu Arg Glu Pro Thr Glu Ser Thr Gln Gln Leu Asn Lys
                    435                 440                 445

Pro Glu Val Leu Glu Val Thr Leu Asn Arg Pro Phe Leu Phe Ala Val
            450                 455                 460

Tyr Asp Gln Ser Ala Thr Ala Leu His Phe Leu Gly Arg Val Ala Asn
    465                 470                 475                 480

Pro Leu Ser Thr Ala
                    485

<210> SEQ ID NO 8
<211> LENGTH: 681
<212> TYPE: DNA
<213> ORGANISM: Homo sapiens
<220> FEATURE:
<221> NAME/KEY: misc_feature
<222> LOCATION: (151)..(531)
<223> OTHER INFORMATION: altenate exon 1 of AGT gene

<400> SEQUENCE: 8
agggcgggga aggggggagg aagggggact gagactctcc tgtttctata tgctatgatg      60
ggatttgacc tgcaattgaa cctttcctca aacacaaggc acaaacctgc cccagcccat     120
catcctccca cagaggcact gtgaatgtat aaagaaaggc gatgctaaga aacgtgctgc     180
aggggaggct ggcacattct gctccttagc taaccgcaca ggcccatggg tccacacaca     240
tcagaccatg gctctctgtg gtctatcttt gccattactt taaccaggct gtttctcatg     300
cgctcatgga gggtgactga agatgccacc ccgaggtgca ccctcagcct cgctggacac     360
ttacggctcg cattctccag ccggaccagg cagttgagga agtcatcgaa gtccagctgg     420
agctcctcat ccgcatacct gagcacaatc agctgcagga ggtggctgct cagctgaaag     480
cctgtgggga caaggagga gacccaggac tcgctgtatc cgagcccga ggtgagtctg       540 cacctttgag ggagctccca ggcagctgag gagagggctc agaagaggaa gccactgttt     600
cactcctcaa agctggggtc cccagaccca gtgggactgc tgcccttggt gtgaatgcag     660
cgtgagagtg tgaatctgtg g                                              681

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:M13 forward
      primer
```

```
<400> SEQUENCE: 9
gttttcccag tcacgacg                                                 18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:M13 reverse
      primer

<400> SEQUENCE: 10
aggaaacagc tatgaccat                                                19

<210> SEQ ID NO 11
<211> LENGTH: 20
<212> TYPE: DNA
<213> ORGANISM: Homo sapiens

<400> SEQUENCE: 11
cctcgaagtg gcctatggaa                                               20

<210> SEQ ID NO 12
<211> LENGTH: 20
<212> TYPE: DNA
<213> ORGANISM: Homo sapiens

<400> SEQUENCE: 12
gcgagactct atgggtgatg                                               20

<210> SEQ ID NO 13
<211> LENGTH: 20
<212> TYPE: DNA
<213> ORGANISM: Homo sapiens

<400> SEQUENCE: 13
gactgagact ctcctgtttc                                               20

<210> SEQ ID NO 14
<211> LENGTH: 19
<212> TYPE: DNA
<213> ORGANISM: Homo sapiens

<400> SEQUENCE: 14
cggggtggca tcttcagtc                                                19

<210> SEQ ID NO 15
<211> LENGTH: 20
<212> TYPE: DNA
<213> ORGANISM: Homo sapiens

<400> SEQUENCE: 15
tggcacattc tgctccttag                                               20

<210> SEQ ID NO 16
<211> LENGTH: 20
<212> TYPE: DNA
<213> ORGANISM: Homo sapiens

<400> SEQUENCE: 16
atacagcgag tcctgggtct                                               20
```

-continued

```
<210> SEQ ID NO 17
<211> LENGTH: 20
<212> TYPE: DNA
<213> ORGANISM: Homo sapiens

<400> SEQUENCE: 17
gaccaggcag ttgaggaagt                                                   20

<210> SEQ ID NO 18
<211> LENGTH: 20
<212> TYPE: DNA
<213> ORGANISM: Homo sapiens

<400> SEQUENCE: 18
gattcacact ctcacgctgc                                                   20

<210> SEQ ID NO 19
<211> LENGTH: 20
<212> TYPE: DNA
<213> ORGANISM: Homo sapiens

<400> SEQUENCE: 19
ccactttcca gcatgttacc                                                   20

<210> SEQ ID NO 20
<211> LENGTH: 20
<212> TYPE: DNA
<213> ORGANISM: Homo sapiens

<400> SEQUENCE: 20
ctgctattcc tcctgatggc                                                   20

<210> SEQ ID NO 21
<211> LENGTH: 20
<212> TYPE: DNA
<213> ORGANISM: Homo sapiens

<400> SEQUENCE: 21
acaggcccat gtgagatatg                                                   20

<210> SEQ ID NO 22
<211> LENGTH: 20
<212> TYPE: DNA
<213> ORGANISM: Homo sapiens

<400> SEQUENCE: 22
tggtattagg gcactgaagg                                                   20

<210> SEQ ID NO 23
<211> LENGTH: 20
<212> TYPE: DNA
<213> ORGANISM: Homo sapiens

<400> SEQUENCE: 23
tgtgttgaag caggatcttc                                                   20

<210> SEQ ID NO 24
<211> LENGTH: 20
<212> TYPE: DNA
<213> ORGANISM: Homo sapiens

<400> SEQUENCE: 24
gatgcaggca ttgaaagatg                                                   20
```

<210> SEQ ID NO 25
<211> LENGTH: 21
<212> TYPE: DNA
<213> ORGANISM: Homo sapiens

<400> SEQUENCE: 25
gtgtttaaca gtctccccag c                                    21

<210> SEQ ID NO 26
<211> LENGTH: 20
<212> TYPE: DNA
<213> ORGANISM: Homo sapiens

<400> SEQUENCE: 26
ctaggtgtgt gacagcctga                                      20

<210> SEQ ID NO 27
<211> LENGTH: 19
<212> TYPE: DNA
<213> ORGANISM: Homo sapiens

<400> SEQUENCE: 27
catgtccctg tggcctctt                                       19

<210> SEQ ID NO 28
<211> LENGTH: 18
<212> TYPE: DNA
<213> ORGANISM: Homo sapiens

<400> SEQUENCE: 28 tgagggtgg ggatggag                                         18

<210> SEQ ID NO 29
<211> LENGTH: 20
<212> TYPE: DNA
<213> ORGANISM: Homo sapiens

<400> SEQUENCE: 29
ctggtcatgt gaaacttacc                                      20

<210> SEQ ID NO 30
<211> LENGTH: 20
<212> TYPE: DNA
<213> ORGANISM: Homo sapiens

<400> SEQUENCE: 30
accttcagct gctccaaaga                                      20

<210> SEQ ID NO 31
<211> LENGTH: 20
<212> TYPE: DNA
<213> ORGANISM: Homo sapiens

<400> SEQUENCE: 31
ccactttcca gcatgttacc                                      20

<210> SEQ ID NO 32
<211> LENGTH: 20
<212> TYPE: DNA
<213> ORGANISM: Homo sapiens

<400> SEQUENCE: 32
ctgctattcc tcctgatggc                                      20

<210> SEQ ID NO 33
<211> LENGTH: 18
<212> TYPE: DNA
<213> ORGANISM: Homo sapiens

<400> SEQUENCE: 33
aaccctcctc tccagcct                                             18

<210> SEQ ID NO 34
<211> LENGTH: 18
<212> TYPE: DNA
<213> ORGANISM: Homo sapiens

<400> SEQUENCE: 34
tcatcaccgt gcctcctc                                             18

<210> SEQ ID NO 35
<211> LENGTH: 20
<212> TYPE: DNA
<213> ORGANISM: Homo sapiens

<400> SEQUENCE: 35
tacttggact ttgggctgag                                           20

<210> SEQ ID NO 36
<211> LENGTH: 21
<212> TYPE: DNA
<213> ORGANISM: Homo sapiens

<400> SEQUENCE: 36
ttgagcaagg cactttgttt c                                         21

<210> SEQ ID NO 37
<211> LENGTH: 21
<212> TYPE: DNA
<213> ORGANISM: Homo sapiens

<400> SEQUENCE: 37
ggctaaatgg tgacagggaa t                                         21

<210> SEQ ID NO 38
<211> LENGTH: 20
<212> TYPE: DNA
<213> ORGANISM: Homo sapiens

<400> SEQUENCE: 38
tagggccttt tcatccacag                                           20

<210> SEQ ID NO 39
<211> LENGTH: 20
<212> TYPE: DNA
<213> ORGANISM: Homo sapiens

<400> SEQUENCE: 39
aatgccggga agcccaaaga                                           20

<210> SEQ ID NO 40
<211> LENGTH: 20
<212> TYPE: DNA
<213> ORGANISM: Homo sapiens

<400> SEQUENCE: 40

| tccaaggctc ccagatagag | 20 |
|---|---|

<210> SEQ ID NO 41
<211> LENGTH: 20
<212> TYPE: DNA
<213> ORGANISM: Homo sapiens

<400> SEQUENCE: 41

| ctctccccaa cggctgtctt | 20 |
|---|---|

<210> SEQ ID NO 42
<211> LENGTH: 20
<212> TYPE: DNA
<213> ORGANISM: Homo sapiens

<400> SEQUENCE: 42

| ctgcacaaac ggctgcttca | 20 |
|---|---|

<210> SEQ ID NO 43
<211> LENGTH: 20
<212> TYPE: DNA
<213> ORGANISM: Homo sapiens

<400> SEQUENCE: 43

| ctctatctgg gagccttgga | 20 |
|---|---|

<210> SEQ ID NO 44
<211> LENGTH: 20
<212> TYPE: DNA
<213> ORGANISM: Homo sapiens

<400> SEQUENCE: 44

| cacagcctgc atgaacctgt | 20 |
|---|---|

<210> SEQ ID NO 45
<211> LENGTH: 20
<212> TYPE: DNA
<213> ORGANISM: Homo sapiens

<400> SEQUENCE: 45

| tgaagcagcc gtttgtgcag | 20 |
|---|---|

<210> SEQ ID NO 46
<211> LENGTH: 19
<212> TYPE: DNA
<213> ORGANISM: Homo sapiens

<400> SEQUENCE: 46

| tccccacttc tcaagggtg | 19 |
|---|---|

<210> SEQ ID NO 47
<211> LENGTH: 20
<212> TYPE: DNA
<213> ORGANISM: Homo sapiens

<400> SEQUENCE: 47

| acaggttcat gcaggctgtg | 20 |
|---|---|

<210> SEQ ID NO 48
<211> LENGTH: 19
<212> TYPE: DNA
<213> ORGANISM: Homo sapiens

<400> SEQUENCE: 48

-continued tccccacttc tcaagggtg                                          19

<210> SEQ ID NO 49
<211> LENGTH: 21
<212> TYPE: DNA
<213> ORGANISM: Homo sapiens

<400> SEQUENCE: 49
tgcctcagtg aactcaaatg g                                       21

<210> SEQ ID NO 50
<211> LENGTH: 20
<212> TYPE: DNA
<213> ORGANISM: Homo sapiens

<400> SEQUENCE: 50 ctcccctcc aaaactacca                                          20

<210> SEQ ID NO 51
<211> LENGTH: 19
<212> TYPE: DNA
<213> ORGANISM: Homo sapiens

<400> SEQUENCE: 51
caggagaatg cagagtggc                                          19

<210> SEQ ID NO 52
<211> LENGTH: 19
<212> TYPE: DNA
<213> ORGANISM: Homo sapiens

<400> SEQUENCE: 52
gcaggcgctc tcagtgaag                                          19

<210> SEQ ID NO 53
<211> LENGTH: 20
<212> TYPE: DNA
<213> ORGANISM: Homo sapiens

<400> SEQUENCE: 53
agcactggag tgacatccag                                         20

<210> SEQ ID NO 54
<211> LENGTH: 20
<212> TYPE: DNA
<213> ORGANISM: Homo sapiens

<400> SEQUENCE: 54
gatggaggac tggtagacag                                         20

<210> SEQ ID NO 55
<211> LENGTH: 20
<212> TYPE: DNA
<213> ORGANISM: Homo sapiens

<400> SEQUENCE: 55 aaggggagg atgacttagt                                          20

<210> SEQ ID NO 56
<211> LENGTH: 21
<212> TYPE: DNA
<213> ORGANISM: Homo sapiens

```
<400> SEQUENCE: 56
gaaattccat ccaaagtcca g                                              21

<210> SEQ ID NO 57
<211> LENGTH: 20
<212> TYPE: DNA
<213> ORGANISM: Homo sapiens

<400> SEQUENCE: 57
gtgcaaggag cataagcctg                                                20

<210> SEQ ID NO 58
<211> LENGTH: 19
<212> TYPE: DNA
<213> ORGANISM: Homo sapiens

<400> SEQUENCE: 58
ctactctccg ctccctctt                                                 19

<210> SEQ ID NO 59
<211> LENGTH: 20
<212> TYPE: DNA
<213> ORGANISM: Homo sapiens

<400> SEQUENCE: 59 aaggggagg atgacttagt                                                 20

<210> SEQ ID NO 60
<211> LENGTH: 21
<212> TYPE: DNA
<213> ORGANISM: Homo sapiens

<400> SEQUENCE: 60
gaaattccat ccaaagtcca g                                              21

<210> SEQ ID NO 61
<211> LENGTH: 17
<212> TYPE: DNA
<213> ORGANISM: Homo sapiens

<400> SEQUENCE: 61
tagccctcag caccctg                                                   17

<210> SEQ ID NO 62
<211> LENGTH: 19
<212> TYPE: DNA
<213> ORGANISM: Homo sapiens

<400> SEQUENCE: 62
tgtccggggt tgttatctg                                                 19

<210> SEQ ID NO 63
<211> LENGTH: 20
<212> TYPE: DNA
<213> ORGANISM: Homo sapiens

<400> SEQUENCE: 63
agaacacagt gcctggcaag                                                20

<210> SEQ ID NO 64
<211> LENGTH: 20
<212> TYPE: DNA
<213> ORGANISM: Homo sapiens
```

```
<400> SEQUENCE: 64
ttcacaaaca agctggtcgg                                                    20

<210> SEQ ID NO 65
<211> LENGTH: 20
<212> TYPE: DNA
<213> ORGANISM: Homo sapiens

<400> SEQUENCE: 65
agtgtttagc gcgggactac                                                    20

<210> SEQ ID NO 66
<211> LENGTH: 20
<212> TYPE: DNA
<213> ORGANISM: Homo sapiens

<400> SEQUENCE: 66
tttggaggct tattgtggca                                                    20

<210> SEQ ID NO 67
<211> LENGTH: 20
<212> TYPE: DNA
<213> ORGANISM: Homo sapiens

<400> SEQUENCE: 67
tgaaagatgc aagcacctga                                                    20

<210> SEQ ID NO 68
<211> LENGTH: 20
<212> TYPE: DNA
<213> ORGANISM: Homo sapiens

<400> SEQUENCE: 68
gaaagcactt tcgtttgcac                                                    20
```

DIABETES GENE

CROSS-REFERENCE TO RELATED APPLICATIONS

Figure 1:
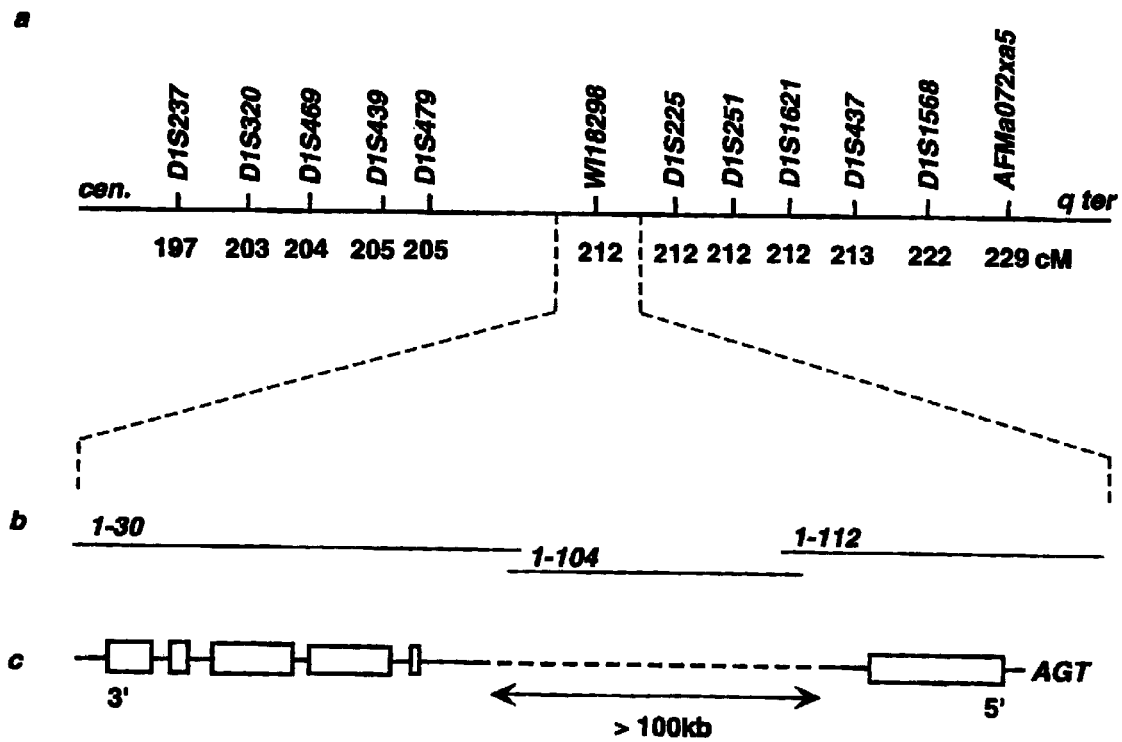

The present application is related to U.S. provisional patent applications Ser. No. 60/135,423 filed 21 May 1999 and Ser. No. 60/174,700 filed 6 Jan. 2000, each incorporated herein by reference.

BACKGROUND OF THE INVENTION

The present invention relates generally to the field of human genetics. Specifically, the present invention relates to methods and materials used to isolate and detect human diabetes mellitus predisposing gene, specifically the angiotensinogen (AGT) gene, some mutant alleles of which cause susceptibility to insulin-dependent diabetes melitus (IDDM). More specifically, the invention relates to germline mutations in the AGT gene and their use in the diagnosis of predisposition to IDDM. The invention also relates to the prophylaxis and/or therapy of diabetes associated with a mutation in the AGT gene. The invention further relates to the screening of drugs for diabetes therapy. Finally, the invention relates to the screening of the AGT gene for mutations, which are useful for diagnosing the predisposition to diabetes.

The publications and other materials used herein to illuminate the background of the invention, and in particular, cases to provide additional details respecting the practice, are incorporated herein by reference, and for convenience, are referenced by author and date in the following text and respectively grouped in the appended List of References.

Diabetes mellitus is among the most common of all metabolic disorders, affecting up to 11% of the population by age 70. Type 1 diabetes (insulin dependent diabetes mellitus or IDDM) represents about 5 to 10% of this group and is the result of a progressive autoimmune destruction of the pancreatic β-cells with subsequent insulin deficiency. IDDM is characterized by a partial or complete inability to produce insulin. Patients with IDDM would die without daily insulin injections to control their disease.

Few advancements in resolving the pathogenesis of diabetes were made until the mid-1970s when evidence began to accumulate to suggest that IDDM had an autoimmune etiopathogenesis. It is now generally accepted that IDDM results from the chronic autoimmune destruction of the insulin producing pancreatic β-cells. Lymphocytes and other inflammatory cells have been observed within the islets of Langerhans in newly diagnosed IDDM patients and have been found preferentially in regenerating islets composed of β-cells rather than those of other cell types. This active immunological process is associated with a variety of autoantibodies to β-cells cytoplasmic and membrane antigens, insulin, and insulin receptors. Although the general mechanism by which IDDM occurs is known, IDDM becomes clinically evident only after the vast majority of pancreatic β-cells have been irrevocably destroyed and the individual becomes dependent upon exogenous insulin.

In both humans and diabetes-prone non-obese diabetic (NOD) mice, genes mapping to the major histocompatibility complex have been associated with susceptibility to IDDM and shown to be very important in the disease process (Todd, 1990). Studies of NOD mice have mapped at least 12 other susceptibility genes to specific chromosomal locations (Prochazaka et al., 1987; Todd et al., 1991; De Gouyon et al., 1993; Morahan et al., 1994; Serreze et al., 1994; Cornall et al., 1991; Garchon et al., 1991). In humans, markers near the insulin/insulin-like growth factor loci have also been associated with IDDM (Bell et al., 1984).

Epidemiological and molecular genetic studies indicate that only 40% of the genetic susceptibility is due to alleles of the MHC class II genes, suggesting additional non-MHC genes are involved (Todd et al., 1988; Buzzetti. et al., 1998). Genome-wide searches and analyses of specific genes have identified more at least 17 loci that contribute to the disease (Buzzetti et al., 1998; Todd, 1995; Concannon et al., 1998; Hashimoto et al., 1994; Davies et al., 1994; Mein et al., 1998; Verge et al., 1998). Significant evidence for linkage was reported for a ~-7 cM region on chromosome 1q42–43 (Concannon et al., 1998). This region of chromosome 1 contains the angiotensinogen (AGY) gene.

Non-insulin dependent diabetes mellitus (NIDDM) is one of the most common inherited diseases in man with an estimated prevalence in Caucasian populations of 8–10% (Harris et al., 1987). It is estimated to affect more than 100 million people worldwide (King and Zimmer, 1988; Harris et al., 1992). Clinically, NIDDM is a heterogenous disorder characterized by chronic hyperglycemia leading to progressive micro- and macrovascular lesions in the cardiovascular, renal and visual systems as well as diabetic neuropathy. The causes of the fasting hyperglycemia and/or glucose intolerance associated with this form of diabetes are not well understood. Unfortunately, the disease is associated with early morbidity and mortality. Subtypes of the disease can be identified based at least to some degree on the time of onset of the symptoms. The principal type of NIDDM occurs at a later time of onset, typically at midlife. Early-onset NIDDM or maturity-onset diabetes of the young (MODY) shares many features with the more common form(s) of NIDDM but onset occurs in early life.

Although most forms of NIDDM do not exhibit simple Mendelian inheritance, the contribution of heredity is well recognized (Rotter et al., 1990). The genetic basis of a few rare monogenic syndromes of NIDDM have been elucidated, but together, these syndromes account for a very small minority of cases (Taylor et al., 1992; Froguel et al., 1993; Steiner et al., 1990; Kadowaki et al., 1994). It is likely that the common forms of NIDDM are complex and heterogenous, and result when a pool of mutant genes, each of which contributes modestly and in a subtle way, interact with each other and with environmental, aging and behavioral influences to lead to the expression of the disease. This pool of genes may vary between populations and among individuals within a population, despite the illusion of a clinically homogenous phenotype.

Certain loci have been linked to rare early-onset forms of Type II diabetes that is associated with chronic hyperglycemia and monogenic inheritance (i.e. maturity onset diabetes of the young (MODY) loci) (Bell et al., 1991; Froguel et al., 1992; Hattersley et al., 1992; Vaxillaire et al., 1995). The defects in the glucokinase (GCK) gene on human chromosome 7 have been found to be responsible for the relatively rare MODY2 phenotype. (Froguel et al., 1992).

The genes responsible for MODY1 and MODY3 have been identified to be transcription factors hepatocyte nuclear factor 4 (HNF4) and hepatocyte nuclear factor 1 HNF1, repsectively. (Yamagata et al., 1996a; Yamagata et al. 1996b). The diabetes gene HNF4/MODY1 regulates expression of the AGT gene (Yanai et al., 1999). Mutations in HNF4/MODY1 have been demonstrated to cause predisposition to maturity onset diabetes of the young.(MODY) a genetically heterogenouse monogenic form of non-insulin-dependent diabetes mellitus (NIDDM) (Yamagata et al., 1996b; Lindner et al., 1997).

Another locus has been identified for a rare early-onset form with mitochondrial inheritance (Van den Ouwenland et al., 1992). In addition, Harris et al. (1996) identified a locus of NIDDM1 on chromosome 2 that appears to play a role in Mexican American diabetes. Further, Mahtani et al. (1996) report evidence of the existence of a gene on human chromosome 12, NIDDM2, that causes NIDDM associated with low insulin secretion. The paper suggests that NIDDM2 and MODY3 represent different alleles of the same gene with severe mutations causing MODY3 and milder mutations giving rise to later-onset NIDDM characterized by low insulin secretion.

In view of the heterogeneity of genes associated with IDDM or NIDDM, it is desired to identify additional genes associated with IDDM or NIDDM for diagnostic and therapeutic purposes.

SUMMARY OF THE INVENTION

Tight linkage between DNA polymorphisms in and near the angiotensinogen (AGT) gene on chromosome 1 and diabetes in particular families was observed (Concannon, 1999). This invention provides the first evidence implicating specific mutations in the AGT gene with susceptibility to IDDM.

Thus, in one aspect of the invention, novel nucleic acids containing additional genornic sequences are provided. These nucleic acids are set forth in SEQ ID NOs: 1–5 and 8.

In a second aspect of the invention, a method for detecting a susceptibility in an individual to insulin-dependent diabetes mellitus is provided. Thus, the present invention provides methods for determining whether a subject is at risk for developing diabetes due to a mutation in the AGT gene. This method relies on the fact that mutations in the AGT have been correlated by the inventors with the disease. It will be understood by those of skill in the art, given the disclosure of the invention that such mutations are associated with a susceptability to diabetes, that a variety of methods may be utilized to detect mutations in the AGT gene, including the mutations disclosed herein, which are associated with a susceptability to IDDM. The method can include detecting, in a tissue of the subject, the presence or absence of a polymorphism of the AGT gene. The detection of a polymorphism in the AGT gene may include ascertaining the existence of at least one of: a deletion of one or more nucleotides; an addition of one or more nucleotides, a substitution of one or more nucleotides; a gross chromosomal rearrangement; an alteration in the level of a messenger RNA transcript; the presence of a non-wild type splicing pattern of a messenger RNA transcript; a non-wild type level of an AGT protein; and/or an aberrant level of an AGT protein.

For example, detecting the polymorphism can include (i) providing a probe/primer comprised of an oligonucleotide which hybridizes to a sense or antisense sequence of an AGT gene or naturally occurring mutants thereof, or 5' or 3' flanking sequences naturally associated with an AGT gene; (ii) contacting the probe/primer to an appropriate nucleic acid containing sample; and (iii) detecting, by hybridization of the probeprimer to the nucleic acid, the presence or absence of the polymorphism; e.g. wherein detecting the polymorphism comprises utilizing the probe/primer to determine the nucleotide sequence of an AGT gene and, optionally, of the flanking nucleic acid sequences. For instance, the primer can be employed in a polymerase chain reaction (PCR), in a ligase chain reaction (LCR) or other amplification reactions known to a skilled artisan. In alternate embodiments, the level of an AGT protein is detected in an immunoassay using an antibody which is specifically immunoreactive with the AGT protein.

In a third aspect of the invention, compounds that are agonists or antagonists of a normal (functional) AGT bioactivity and their use in preventing or treating diabetes are provided. For example, to ameliorate disease symptoms involving insufficient expression of an AGT gene and/or inadequate amount of functional AGT bioactivity in a subject, a gene therapeutic (comprising a gene encoding a functional AGT protein) or a protein therapeutic (comprising a functional AGT protein or fragment thereof can be administered to the subject. Alternatively, agonists or antagonists of AGT function (wild-type or mutant) or an AGT receptor or a receptor for fragments of AGT can be administered.

In a fourth aspect of the invention, compounds that are antagonists of a disease causing AGT bioactivity and their use in preventing or treating diabetes are provided. For example, to ameliorate disease symptoms involving expression of a mutant AGT gene or aberrant expression of a normal AGT gene in a subject, a therapeutically effective amount of an antisense, ribozyme or triple helix molecule to reduce or prevent gene expression may be administered to the subject. Alternatively, to ameliorate disease symptoms involving the regulation via an AGT protein or AGT protein fragments of an upstream or downsteam element in an AGT mediated biochemical pathway (e.g. signal transduction), a therapeutically effective amount of an agonist or antagonist compound (e.g. small molecule, peptide, peptidomimetic, protein or antibody) that can prevent normal binding of the wildtype AGT protein, can induce a therapeutic effect.

In another aspect of the invention, assays, e.g., for screening test compounds to identify antagonists (e.g. inhibitors), or alternatively, agonists (e.g. potentiators), of an interaction between an AGT protein and, for example, a protein or nucleic acid that binds to the AGT protein or fragments of AGT are provided. An exemplary method includes the steps of (i) combining an AGT polypeptide or bioactive fragments thereof, an AGT target molecule (such as an AGT ligand or nucleic acid), and a test compound, e.g., under conditions wherein, but for the test compound, the AGT protein and AGT target molecule are able to interact; and (ii) detecting the formation of a complex which includes the AGT protein and the target molecule either by directly quantitating the complex or by measuring inductive effects of the AGT protein or fragments of AGT protein. A statistically significant change, such as a decrease, in the interaction of the AGT and AGT target molecule in the presence of a test compound (relative to what is detected in the absence of the test compound) is indicative of a modulation (e.g., inhibition or potentiation of the interaction between the AGT protein or fragments of the AGT protein and the target molecule).

In a further aspect of the present invention concerns methods for modulating the transcription of certain genes in a cell by modulating AGT bioactivity, (e.g., by potentiating or disrupting an AGT bioactivity). In general, whether carried out in vivo, in vitro, or in situ, the method comprises treating the cell with an effective amount of an AGT therapeutic (agonist or antagonist of an AGT bioactivity) so as to alter, relative to the cell in the absence of treatment, the level of transcription of certain genes. Accordingly, the method can be carried out with AGT therapeutics such as peptide and peptidomimetic or other molecules identified in the above-referenced drug screens which agonize or antagonize the effects of a AGT bioactivity (e.g. transcription) of a gene which is regulated by an AGT protein. Other AGT therapeutics include antisense constructs for inhibiting expression of AGT proteins, and dominant negative mutants of AGT proteins which competitively inhibit interactions between ligands (e.g. proteins) and nucleic acids upstream and downstream of the wild-type AGT protein.

BRIEF DESCRIPTION OF THE FIGS.

FIGS. 1A–1C show a physical map of the AGT region. FIG. 1A: Microsatellite markers used in genotyping. The STS WI18298 used to screen the BAC library lies on BAC 1–30. FIG. 1B: BACs containing the AGTgene. FIG. 1C: structure of AGT and alignment on BAC contig.

Figure 2:
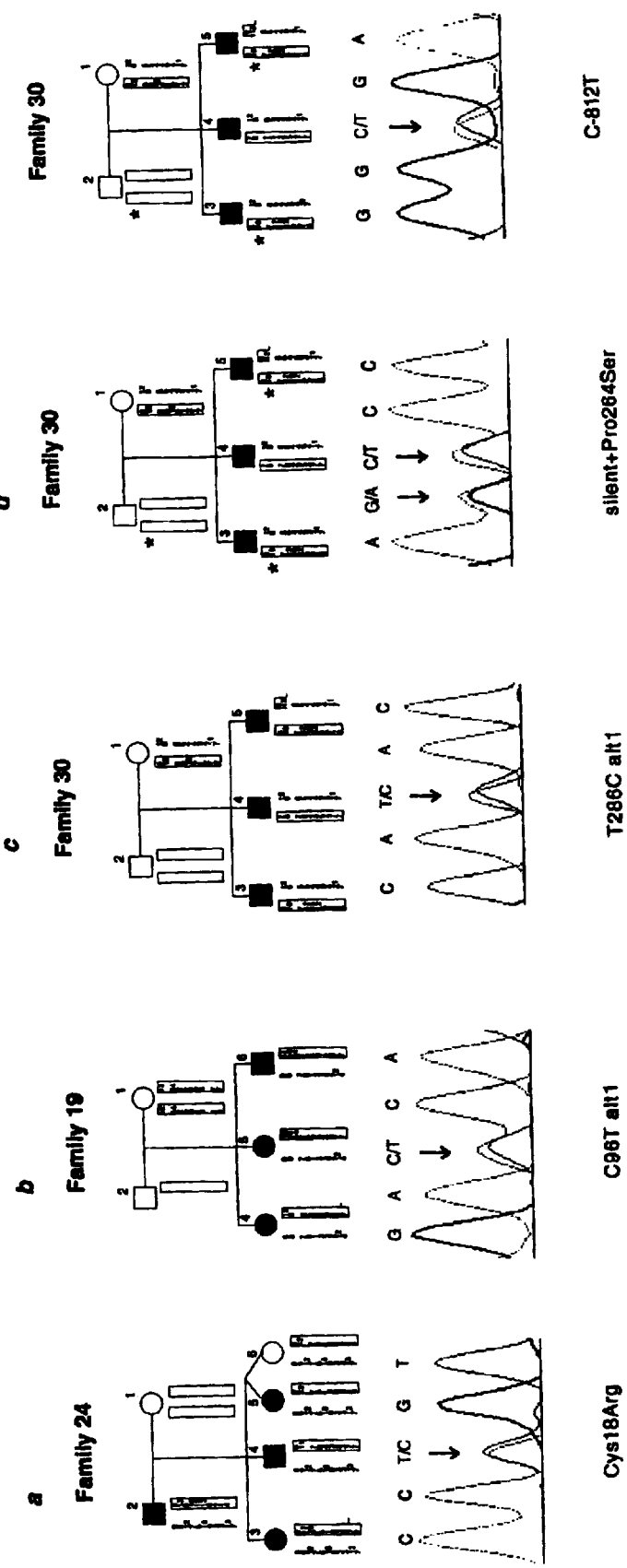

FIGS. 2A–2E show haplotypes and segregation of AGT mutations in multiplex type 1 diabetes families. Shared haplotypes are in shaded boxes. FIG. 2A: Cys18 Arg. FIG. 2B: (96)T in alternative exon 1. FIG. 2C: T(286)C in alternative exon 1. FIG. 2D: Pro264Ser linked to a silent polymorphism is present on the haplotype with the asterisk in family 30. FIG. 2E: C(811)T is on the same haplotype in family 30 as Pro264Ser.

FIGS. 3A–3C show rare polymorphisms in AGT and expression of alternatively spliced transcripts. FIG. 3A: Genomic organization of AGT and position of rare polymorphisms found in diabetes mellitus families. Approximate positions of promoters for the alternative and published transcripts are indicated by large arrows. The positions and types of rare polymorphisms identified in multiplex diabetes families are indicated above the exons. Within the coding exons the numbers refer to the base pair position in the cDNA. The polymorphism at −811 is relative to the published transcription start site in exon I (Gaillard et al., 1989). A schematic of the AGT polypeptide is shown below. The positions of the amino acid substitutions caused by the polymorphisms are indicated relative to the start of the mature peptide. Coding region of AGT (black box); signal sequence(ss) (gray box); Ang I precursor peptide to the octapeptide Ang II (black box); mature peptide (black box and hatched box). Greater than 100 kb of genomic DNA (dashed line). All Cys positions of AGT indicated in a circle. FIG. 3B: Alignment of angiotensinogen from human, gorilla, chimpanzee, rat, sheep, and mouse (SEQ ID Nos. 69–80) is shown. Cys18 in bold; Asn137-Cys138-Thr139 underlined. FIG. 3C: Alignment of additional missense mutations: Ala122, Pro264, Asp319, and Ala401 (SEQ ID Nos. 81–104) shown in bold.

DETAILED DESCRIPTION OF THE INVENTION

The present invention is based in part on the discovery of polymorphisms in the AGT gene which are linked to insulin-dependent diabetes mellitus. Based on this finding the invention provides therapeutic methods, compositions and diagnostics for diabetes based on AGT.

The cDNA for the AGT gene and the protein sequence are set forth in GenBank accession numbers K02215 and AH002594. The latter accession shows some genomic sequences (about 40–60 nucleotides) surrounding the 5 exons of the AGT gene. The AGT gene comprises 5 exons which are shown in SEQ ID NOS:1–5, along with genomic intron or untranslated sequences. SEQ ID NOs: 1–5 contain additional genomic sequences not previously disclosed. The AGT gene encodes a protein which comprises a 33 amino acid signal peptide and a 452 amino acid mature peptide. The coding sequence for AGT compiled from the exons in SEQ ID NOs:1–5 is shown in SEQ ID NO:6. The corresponding amino acid sequence for AGT is set forth in SEQ ID NO:7. The sequence of alternate exon 1 along with surrounding genomic intron or untranslated sequences is shown in SEQ ID NO:8.

The present invention relates to AGT agonists and antagonists and their use in treating diabetes. For example, (i) nucleic acid molecules encoding functional AGT protein; (ii) nucleic acids that are effective antisense, ribozyme and triplex antagonists of nucleic acids encoding functional AGT protein; (iii) functional AGT proteins or peptides; (iv) anti-AGT antibodies; (v) drugs affecting wild-type or mutant AGT function or AGT interaction with an AOT receptor and preparations of such compositions are disclosed herein. In addition, the invention provides drug discovery assays for identifying additional agents that agonize or antagonize the biological function of AGT protein (e.g. by altering the interaction of AGT molecules with either downstream or upstream elements in the biochemical (e.g. signal transduction) pathway). Moreover, the present invention provides assays for diagnosing whether a subject has or has a predisposition towards developing diabetes mellitus.

Proof that any particular gene located within the genetically defined interval is a disease susceptability locus is obtained by finding sequences in DNA or RNA extracted from affected kindred members which create abnormal gene products or abnormal levels of gene product Such disease susceptibility alleles will co-segregate with the disease in large kindreds. They will also be present at a much higher frequency in non-kindred individuals with the disease than in individuals in the general population. In identifying a disease susceptability locus, the key is to find polymorphisms or mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary, tertiary or quaternary protein structure. Small deletions or base pair substitutions could also significantly alter protein expression by changing the level of transcription, splice pattern, mRNA stability, or translation efficiency of the gene transcript. Silent mutations or those resulting in conservative amino acid substitutions would not generally be expected to disrupt protein function. Causal mutations can also be found in the promoter of the gene. These mutations would interfere with the binding of regulatory factors and in this way alter transcription of the gene and therefore change the function of the gene.

In one aspect, the invention features probes and primers for use in a prognostic or diagnostic assay. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence of AGT, including 5' and/or 3' untranslated regions. In preferred embodiments, the probe further comprises a label group attached thereto and able to be detected, e.g. the label group is selected from amongst radioisotopes, fluorescent compounds, enzymes, and enzyme co-factors.

In a further aspect, the present invention features methods for determining whether a subject is at risk for developing diabetes mellitus. According to the diagnostic and prognostic methods of the present invention, alteration of the wild-type AGT locus is detected. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Point mutations or deletions in the promoter can change transcription and thereby alter the gene function. Somatic mutations are those which occur only in certain tissues and are not inherited in the genrline. Germline mutations can be found in any of a body's tissues and are inherited. The finding of AGT germline mutations thus provides diagnostic information. An AGT allele which is not deleted (e.g., found on the sister chromosome to a chromosome carrying an AGT deletion) can be screened for other mutations, such as insertions, small deletions, and point mutations. Point mutational events may occur in regulatory regions, such as in the promoter of the gene, or in intron regions or at intron/exon junctions.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology. In addition to the techniques described herein, similar and other useful techniques are also described in U.S. Pat. Nos. 5,837,492 and 5,800,998, each incorporated herein by reference.

Predisposition to disease can be ascertained by testing any tissue of a human for mutations of the AGT gene. For example, a person who has inherited a germline AGT mutation would be prone to develop IDDM. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the AGT gene. Alteration of a wild-type AGT allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. For a gene as large as AGT, manual sequencing is very labor-intensive, but under optimal conditions, mutations in the coding sequence of a gene are rarely missed. nother approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation.

Detection of point mutations may be accomplished by molecular cloning of the AGT allele(s) and sequencing the allele(s) using techniques well known in the art. Alternatively, the gene sequences can be amplified directly from a genomic DNA preparation from the tissue, using known techniques. The DNA sequence of the amplified sequences can then be determined.

There are six well known methods for a more complete, yet still indirect, test for confirming the presence of a susceptibility allele: 1) single-stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al, 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Rano and Kidd, 1989). For allele-specific PCR, primers are used which hybridize at their 3' ends to a particular AGT mutation. If the particular AGT mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the AGT mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type AGT gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the fill length duplex RNA for the riboprobe and the mRNA or DNA. The riboprobe need not be the full length of the AGT mRNA or gene but can be a segment of either. If the riboprobe comprises only a segment of the AGT mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al, 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR before hybridization. Changes in DNA of the AGT gene can also be detected using Southern hybridization, especially if the changes are gross rearrangements, such as deletions and insertions.

DNA sequences of the AGT gene which have been amplified by use of PCR may also be screened using allele-specific probes. These probes are nucleic acid oligomers, each of which contains a region of the AGT gene sequence harboring a known mutation. For example, one oligomer may be about 30 nucleotides in length (although shorter and longer oligomers are also usable as well recognized by those of skill in the art), corresponding to a portion of the AGT gene sequence. By use of a battery of such allele-specific probes, PCR amplification products can be screened to identify the presence of a previously identified mutation in the AGT gene. Hybridization of allele-specific probes with amplified AGT sequences can be performed, for example, on a nylon filter. Hybridization to a particular probe under high stringency hybridization conditions indicates the presence of the same mutation in the tumor tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic AGT sequences from disease patients with those from a control population. Alternatively, one could sequence messenger RNA after amplification, e.g., by PCR, thereby eliminating the necessity of determining the exon structure of the candidate gene.

Mutations from disease patients falling outside the coding region of AGT can be detected by examining the non-coding regions, such as introns and regulatory sequences near or within the AGT gene. An early indication that mutations in noncoding regions are important may come from Northern blot experiments that reveal messenger RNA molecules of abnormal size or abundance in disease patients as compared to control individuals.

Alteration of AGT mRNA expression can be detected by any techniques known in the art. These include Northern blot analysis, PCR amplification and RNase protection. Diminished or increased mRNA expression indicates an alteration of the wild-type AGT gene. Alteration of wild-type AGT genes can also be detected by screening for alteration of wild-type AGT protein. For example, monoclonal antibodies immunoreactive with AGT can be used to screen a tissue. Lack of cognate antigen would indicate an AGT mutation. Antibodies specific for products of mutant alleles could also be used to detect mutant AGT gene product. Such immunological assays can be done in any convenient formats known in the art. These include Western blots, immunohistochemical assays and ELISA assays. Any means for detecting an altered AGT protein can be used to detect alteration of wild-type AGT genes. Functional assays, such as protein binding determinations, can be used. In addition, assays can be used which detect AGT biochemical function. Finding a mutant AGT gene product indicates alteration of a wild-type AGT gene.

The primer pairs of the present invention are useful for determination of the nucleotide sequence of a particular AGT allele using PCR. The pairs of single-stranded DNA primers can be annealed to sequences within or surrounding the AGT gene on chromosome 1 in order to prime amplifying DNA synthesis of the AGT gene itself A complete set of these primers allows synthesis of all of the nucleotides of the AGT gene coding sequences, i.e., the exons. The set of primers preferably allows synthesis of both intron and exon sequences. Allele-specific primers can also be used. Such primers anneal only to particular AGT mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from AGT sequences or sequences adjacent to AGT, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the known sequences of the AGT exons and the 5' alternate exon, the design of particular primers is well within the skill of the art. Suitable primers for mutation screening are also described herein.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the AGT gene or mRNA using other techniques.

It has been discovered that individuals with the wild-type AGT gene do not have IDDM which results from the AGT allele. However, mutations which interfere with the function of the AGT protein are involved in the susceptability to IDDM as shown herein. Thus, the presence of an altered (or a mutant) AGT gene which produces a protein having a loss of function, or altered function, directly correlates to an increased risk of disease. In order to detect an AGT gene mutation, a biological sample is prepared and analyzed for a difference between the sequence of the AGT allele being analyzed and the sequence of the wild-type AGT allele. Mutant AGT alleles can be initially identified by any of the techniques described above. The mutant alleles are then sequenced to identify the specific mutation of the particular mutant allele. Alternatively, mutant AGT alleles can be initially identified by identifying mutant (altered) AGT proteins, using conventional techniques. The mutant alleles are then sequenced to identify the specific mutation for each allele. The mutations, especially those which lead to an altered function of the AGT protein, are then used for the diagnostic methods of the present invention.

The present invention employs definitions commonly used in the art with specific reference to the gene described in the present application. Such definitions can be found in U.S. Pat. Nos. 5,837,492 and 5,800,998, each incorporated herein by reference. Such definitions are employed herein unless the context indicates otherwise.

Methods of Use: Nucleic Acid Diagnosis and Diagnostic Kits

In order to detect the presence of an AGT allele predisposing an individual to diabetes, a biological sample such as blood is prepared and analyzed for the presence or absence of predisposing alleles of AGT. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis. Diagnositic or prognostic tests can be performed as described herein or using well known techniques, such as described in U.S. Pat. No. 5,800,998, incorporated herein by reference.

Initially, the screening method involves amplification of the relevant AGT sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for diabetes susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 1. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mittlin, 1989; U.S. Pat. No. 4,868,105, and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding AGT. Allele specific probes are also contemplated within the scope of this example and exemplary allele specific probes include probes encompassing the predisposing or potentially predisposing mutations summarized in herein.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting AGT. Thus, in one example to detect the presence of AGT in a cell sample, more than one probe complementary to AGT is employed and in particular the number of different probes is alternatively 2, 3, or 5 different nucleic acid probe sequences. In another example, to detect the presence of mutations in the AGT gene sequence in a patient, more than one probe complementary to AGT is employed where the cocktail includes probes capable of binding to the allele-specific mutations identified in populations of patients with alterations in AGT. In this embodiment, any number of probes can be used, and will preferably include probes corresponding to the major gene mutations identified as predisposing an individual to diabetes. Some candidate probes contemplated within the scope of the invention include probes that include the allele-specific mutations identified herein and those that have the AGT regions corresponding to SEQ ID NOs:1–5 and 8 both 5' and 3' to the mutation site.

Methods of Use: Peptide Diagnosis and Diagnostic Kits

Susceptibility to daibetes can also be detected on the basis of the alteration of wild-type AGT polypeptide. Peptide diagnositic or prognostic tests can be performed as described herein or using well known techniques, such as described in U.S. Pat. No. 5,800,998, incorporated herein by reference. For example, such alterations can be determined by sequence analysis in accordance with conventional techniques. More preferably, antibodies (polyclonal or monoclonal) are used to detect differences in, or the absence of, AGT peptides. The antibodies may be prepared in accordance with conventional techniques. Other techniques for raising and purifying antibodies are well known in the art and any such techniques may be chosen to achieve the preparations claimed in this invention. In a preferred embodiment of the invention, antibodies will immunoprecipitate AGT proteins or fragments of the AGT protein from solution as well as react with AGT peptides on Western or immunoblots of polyacrylamide gels. In another preferred embodiment, antibodies will detect AGT proteins and protein fragments in paraffin or frozen tissue sections, using immunocytochemical techniques.

Preferred embodiments relating to methods for detecting AGT or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al. in U.S. Pat. Nos. 4,376,110 and 4,486,530, hereby incorporated by reference.

Methods of Use: Drug Screening

This invention is particularly useful for screening compounds by using a wild-type or mutant AGT polypeptide or binding fragment thereof in any of a variety of drug screening techniques. Drug screening can be performed as described herein or using well known techniques, such as described in U.S. Pat. Nos. 5,800,998 and 5,891,628, each incorporated herein by reference.

The AGT polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an AGT polypeptide or fragment and the agent being tested, or examine the degree to which the formation of a complex between an AGT polypeptide or fragment and a known ligand, e.g. AGT receptor (AT1), is interfered with by the agent being tested.

Thus, the present invention provides methods of screening for drugs comprising contacting such an agent with an AGT polypeptide or fragment thereof and assaying (i) for the presence of a complex between the agent and the AGT polypeptide or fragment, or (ii) for the presence of a complex between the AGT polypeptide or fragment and a ligand, by methods well known in the art. In such competitive binding assays the AGT polypeptide or fragment is typically labeled. Free AGT polypeptide or fragment is separated from that present in a protein:protein complex, and the amount of free (i.e., uncomplexed) label is a measure of the binding of the agent being tested to AGT or its interference with AGT:ligand binding, respectively.

Another technique for drug screening provides high throughput screening for compounds having suitable binding affinity to the AGT polypeptides and is described in detail in Geysen, PCT published application WO 84/03564, published on Sep. 13, 1984. Briefly stated, large numbers of different small peptide test compounds are synthesized on a solid substrate, such as plastic pins or some other surface. The peptide test compounds are reacted with AGT polypeptides and washed. Bound AGT polypeptides are then detected by methods well known in the art.

Purified AGT can be coated directly onto plates for use in the aforementioned drug screening techniques. However, non-neutralizing antibodies to the polypeptide can be used to capture antibodies to immobilize the AGT polypeptide on the solid phase.

This invention also contemplates the use of competitive drug screening assays in which neutralizing antibodies capable of specifically binding the AGT polypeptide compete with a test compound for binding to the AGT polypeptide or fragments thereof. In this manner, the antibodies can be used to detect the presence of any peptide which shares one or more antigenic determinants of the AGT polypeptide.

A further technique for drug screening involves the use of host eukaryotic cell lines or cells (such as described above) which express a wild-type or mutant AGT gene and as a consequence of expression of wild type or mutant AGT demonstrate a specific phenotype. The phenotype of the cells is examined to determine if the compound is capable of modulating the phenotype and thereby AGT function.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et at., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an AGT specific binding partner, or to find mimetics of an AGT polypeptide.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. Rational drug design can be performed as described herein or using well known techniques, such as described in U.S. Pat. Nos. 5,800,998 and 5,891,628, each incorporated herein by reference.

In one approach, one first determines the three-dimensional structure of a protein of interest (e.g., AGT polypeptide or fragments of the AGT polypeptide) or, for example, of the AGT-receptor or ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., AGT polypeptide or fragments thereof) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore. Thus, one may design drugs which have, e.g., improved AGT polypeptide activity or stability or which act as inhibitors, agonists, antagonists, etc. of AGT polypeptide activity.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment or prophylaxis of diabetes, use of such a substance in the manufacture of a composition for administration, e.g., for treatment or prophylaxis of diabetes, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Based Therapies

According to the present invention, a method is also provided of supplying wild-type AGT function to a cell which carries mutant AGT alleles. The wild-type AGT gene or a part of the gene may be introduced into the cell in a vector such that the gene remains extrachromosomal. In such a situation, the gene will be expressed by the cell from the extrachromosomal location. If a gene fragment is introduced and expressed in a cell carrying a mutant AGT allele, the gene fragment should encode a part of the AGT protein which is required for normal physiological processes of the cell. More preferred is the situation where the wild-type AGT gene or a part thereof is introduced into the mutant cell in such a way that it recombines with the endogenous mutant AGT gene present in the cell. Such recombination requires a double recombination event which results in the correction of the AGT gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of the routineer. See also U.S. Pat. Nos. 5,800,998 and 5,891,628, each incorporated by reference herein.

Among the compounds which may exhibit anti-diabetes activity are antisense, ribozyme, and triple helix molecules. Such molecules may be designed to reduce or inhibit mutant AGT activity. Techniques for the production and use of such molecules are well known to those of skill in the art, such as described herein or in U.S. Pat. No. 5,800,998, incorporated herein by reference.

Antisense RNA and DNA molecules act to directly block the translation of mRNA by binding to targeted mRNA and preventing protein translation. With respect to antisense DNA, oligodeoxyribonucleotides derived from the translation initiation site, e.g., between the −10 and +10 regions of the AGT nucleotide sequence of interest, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. The composition of ribozyme molecules must include one or more sequences complementary to the target AGT mRNA, preferably the mutant AGT mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding AGT, preferably mutant AGT proteins.

Specific ribozyme cleavage sites within any potential RNA target are initially identified by scanning the target molecule for ribozyme cleavage sites which include the following sequence: GUA, GUU and GUC. Once identified, short RNA sequences of between 15 and ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays.

Nucleic acid molecules to be used in triplex helix formation should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC.sup.+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of guanidine residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'–3', 3'–5' manner, such that they base pair with one strand of a duplex first and then the other, eliminating the necessity for a sizeable stretch of either purines or pyrimidines to be present on one strand of a duplex.

It is possible that the antisense, ribozyme, and/or triple helix molecules described herein may reduce or inhibit the translation of mRNA produced by both normal and mutant AGT alleles. In order to ensure that substantial normal levels of AGT activity are maintained in the cell, nucleic acid molecules that encode and express AGT polypeptides exhibiting normal AGT activity may be introduced into cells which do not contain sequences susceptible to whatever antisense, ribozyme, or triple helix treatments. Such sequences may be introduced via gene therapy methods. Alternatively, it may be preferable to coadminister normal AGT protein into the cell or tissue in order to maintain the requisite level of cellular or tissue AGT activity.

Antisense RNA and DNA molecules, ribozyme molecules and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include, but are not limited to, the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

Gene therapy would be carried out according to generally accepted methods, for example, as described in further detail in U.S. Pat. Nos. 5,837,492 and 5,800,998 and references cited therein, all incorporated by reference herein. Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences conventionally used.

Methods of Use: Peptide Therapy

Peptides which have AGT activity can be supplied to cells which carry mutant or missing AGT alleles. Peptide therapy is performed as described herein or using well known techniques, such as described in U.S. Pat. Nos. 5,800,998 and 5,891,628, each incorporated herein by reference.

Protein can be produced by expression of the cDNA sequence in bacteria, for example, using known expression vectors. Alternatively, AGT polypeptide can be extracted from AGT-producing mammalian cells. In addition, the techniques of synthetic chemistry can be employed to synthesize AGT protein. Any of such techniques can provide the preparation of the present invention which comprises the AGT protein. Preparation is substantially free of other human proteins. This is most readily accomplished by synthesis in a microorganism or in vitro.

Active AGT molecules can be introduced into cells by microinjection or by use of liposomes, for example. Alternatively, some active molecules may be taken up by cells, actively or by diffusion. Extracellular application of the AGT gene product may be sufficient to affect the development and or progression of diabetes. Supply of molecules with AGT activity should lead to partial reversal of the diabetic phenotype. Other molecules with AGT activity (for example, peptides, drugs or organic compounds) may also be used to effect such a reversal. Modified polypeptides having substantially similar function are also used for peptide therapy.

Alternatively, antibodies that are both specific for mutant AGT gene product and interfere with its activity may be used. Such antibodies may be generated using standard techniques described herein or using conventional techniques, such as described in U.S. Pat. Nos. 5,837,492; 5,800,998 and 5,891,628, against the proteins themselves or against peptides corresponding to the binding domains of the proteins. Such antibodies include but are not limited to polyclonal, monoclonal, Fab fragments, F(ab').sub.2 fragments, single chain antibodies, chimeric antibodies, humanized antibodies etc.

Methods of Use: Agonists or Antagonists for Diabetes Prevention or Treatment

Mutations in angiotensinogen predisposing to diabetes suggest that the protein or peptide fragments of the protein have roles in the development or continued functioning of the beta islet cells of the pancreas. It is known from the literature that mutation of Cys18 leads to a reduction of the cleavage of angiotensinogen by renin (Rosa et al., 1998). However, there are a series of experiments which would be necessary in order to address angiotensinogen's role in the disease and to identify points for pharmacological intervention.

The only known peptide derived by cleavage of angiotensinogen with renin is angiotensin 1. Angiotensin 1 (AI) is then subsequently cleaved by angiotensin converting enzyme (ACE) to angiotensin 2 (AII) which is, itself, metabolized to angiotensin 3 (AIII) and smaller peptides. Two human receptors for angiotensin 2, AT1 and AT2, are known in the literature, but it has been reported that other receptors for these active metabolites exist (for example, Kozlowski et al., 1993), and can be molecularly cloned. These receptors may have a biological distribution that includes the pancreas and/or be selective for one or more of the angiotensin 1 metabolites. Such receptors represent good targets for pharmacological intervention in diabetes. Equally, agonists, for example AI, AII, AIII or synthetic derivatives such as those described by Samanen et al. (1991), or antagonists of the known angiotensin receptors (e.g., losartan) represent drugs for use in the treatment or prevention of diabetes. After the initial cleavage by renin a large polypetide remains. The breakdown of this polypeptide into other active fragments can be envisioned. Agonist and antagonists of the receptors for these fragments as well as the proteases responsible for there formation also represent drugs for the treatment or prevention of diabetes.

Methods of Use: Identification of Functional Peptides Derived From AGT

Nothing, in current literature, is known of the metabolic fate of the remainder of angiotensinogen once angiotensin 1 is cleaved off by renin. It is possible that this protein has a direct biological function or be cleaved to bio-active peptides. The existence of such peptides can be confirmed by using a panel of polyclonal antibodies which bind to angiotensingen and use these antibodies to look for immunoreactive peptide fragments in human or other animal sera. Once such peptides are identified, their cognate receptors can be cloned using standard molecular biology approaches. Another approach would be to screen for receptor partners for random fragments of angiotensinogen using the yeast two hybrid system or other techniques to discover protein/protein interactions. The peptides, identified by any approach, may, themselves, have utility as drugs for the treatment of diabetes or their receptors may represent points for pharmacological intervention in diabetes. In addition the inhibitors or activators of the protease (s) responsible for the cleavage of the full length AGT protein represnet another opportunity to develop drugs to treat or prevent diabetes.

Methods of Use: Transformed Hosts: Transgenic/Knockout Animals and Models

Similarly, cells and animals which carry a mutant AGT allele can be used as model systems to study and test for substances which have potential as therapeutic agents. These may be isolated from individuals with AGT mutations, either somatic or germline. Alternatively, the cell line can be engineered to carry the mutation in the AGT allele, as described above. After a test substance is applied to the cells, the phenotype of the cell is determined. Any trait of the transformed cells can be assessed using techniques well known in the art. Transformed hosts, transgenic/knockout animals and models are prepared and used as described herein or using well known techniques, such as described in U.S. Pat. Nos. 5,800,998 and 5,891,628, each incorporated herein by reference.

Animals for testing therapeutic agents can be selected after mutagenesis of whole animals or after treatment of germline cells or zygotes. Such treatments include insertion of mutant AGT alleles, usually from a second animal species, as well as insertion of disrupted homologous genes. Alternatively, the endogenous AGT gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992) to produce knockout or transplacement animals. A transplacement is similar to a knockout because the endogenous gene is replaced, but in the case of a transplacement the replacement is by another version of the same gene. After test substances have been administered to the animals, the the diabetic phenotypemust be assessed. If the test substance prevents or suppresses thethe diabetic phenotype, then the test substance is a candidate therapeutic agent for the treatment of diabetes. These animal models provide an extremely important testing vehicle for potential therapeutic products.

In one embodiment of the invention, transgenic animals are produced which contain a functional transgene encoding a functional AGT polypeptide or variants thereof. Transgenic animals expressing AGT transgenes, recombinant cell lines derived from such animals and transgenic embryos may be useful in methods for screening for and identifying agents that induce or repress function of AGT. Transgenic animals of the present invention also can be used as models for studying indications such as IDDM.

In one embodiment of the invention, a AGT transgene is introduced into a non-human host to produce a transgenic animal expressing a human, murine or other species AGT gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous AGT by homologous recombination between the transgene or a mutant gene and the endogenous gene; or the endogenous gene may be eliminated by deletion as in the preparation of "knock-out" animals. Typically, a AGT gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress AGT or express a mutant form of the polypeptide. Alternatively, the absence of a AGT in "knock-out" mice permits the study of the effects that loss of AGT protein has on a cell in vivo. Knock-out mice also provide a model for the development of AGT-related diabetes.

Methods for producing knockout animals are generally described by Shastry (1995, 1998) and Osterrieder and Wolf (1998). The production of conditional knockout animals, in which the gene is active until knocked out at the desired time is generally described by Feil et al. (1996), Gagneten et al. (1997) and Lobe and Nagy (1998). Each of these references is incorporated herein by reference.

As noted above, transgenic animals and cell lines derived from such animals may find use in certain testing experiments. In this regard, transgenic animals and cell lines capable of expressing wild-type or mutant AGT may be exposed to test substances. These test substances can be screened for the ability to alter expression of wild-type AGT or alter the expression or function of mutant AGT.

Pharmaceutical Compositions and Routes of Administration

The AGT polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be nontoxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Hogan et al., Manipulating the Mouse Embryo, (Cold Spring Harbor Laboratory Press, Cold Spring Harbor, N.Y., 1986). A general discussion of techniques and materials for human gene mapping, including mapping of human chromosome 1, is provided, e.g., in White and Lalouel, 1988.

EXAMPLES

The present invention is described by reference to the following Examples, which are offered by way of illustration and are not intended to limit the invention in any manner. Standard techniques well known in the art or the techniques specifically described below were utilized.

Example 1

Methods

Subjects, genotyping, and haplotype analyses. The families used in this study are part of a collection of IDDM families at the Human Biological Data Interchange (HBDI), Philadelphia, Pa. Genomic DNA samples were ordered from the HBDI Repository located at the Coriell Institute for Medical Research in Camden, N.J. In the initial part of this study samples were ordered for individuals from 38 nuclear families with 3 siblings affected with IDDM. After identification of sequence variants in this first set of families, an additional 308 unrelated individuals with IDDM were obtained from HBDI. The initial control set of 120 samples were the grandparents of the Utah families included in the Centre d'Etude du Polymorphisme Humain. (CEPH) database. Unrelated spouses from other Utah families were used as additional controls. No information on the presence or absence of diabetes in these samples was available. Genotypes using fluorescently labelled primers were determined for 11 simple tandem repeat polymorphisms spanning the published IDDM linkage on chromosome 1q (Concannon et al., 1998). Marker positions and primer sequences were obtained from Genethon (D1S237, D1S469, D1S439, D1S479, D1S437, D1S225, D1S251, D1S1568, AFMa072xa5x1), Marshfiel (D1S320), and CHLC (D1S1621). Haplotype analysis was performed by using the program MCLINK (Thomas et al., 1999). Comparisons of observed frequencies of mutation in cases and controls were made with a chi-squared, log likelihood ratio, test. The null hypothesis is that the observations come from Binomial distributions with the same probability parameters. The p-value quoted for each comparison is that for rejection of the null hypothesis in favor of the alternative hypothesis that the Binomials have unequal probability parameters.

Genomic sequencing and mutation detection. A human genomic BAC library (Research Genetics) was screened by PCR for clones containing the marker WI18298. The end sequences of BAC 1–30 were used as probes to assemble a BAC contig. 6× genomic sequencing coverage of BACs 1–30, 1–104 and 1–112 was obtained by sequencing of plasmid libraries constructed with randomly sheared and Sau3A-digested BAC DNA. For mutation detection exons were amplified from genomic DNA with primers placed in intronic sequences flanking each exon. Nested amplifications were performed with primers containing M13 forward (5'-G-GTTTTCCCAGTCACGACG-3'; SEQ ID NO:9) and reverse (5'-AGGAAACAGCTATGAC CAT-3'; SEQ ID NO:10) universal primer sequences at the 5' termini. Nested PCR products were cycle sequenced directly and run on ABI 377 automated sequencers (Perkin-Elmer). Sequence data were analyzed for polymorphisms using software developed at Myriad Genetics, Inc.

GenBank accession numbers. Human AGT retina EST, AA059356; human AGT M24689; rat AGT L00094; sheep AGT D17520; mouse AGT AF045887; gorilla AGT 188488; chimpanzee AGT 188487. The sequences of AGT for gorilla and chimpanzee were generated in this study.

Example 2

Association of AGT Gene and IDDM

To investigate whether mutations in AGT are responsible for the reported linkage of type 1 diabetes to the chromosomal region 1q42–43, we carried out a three stage analysis. Initially we obtained a set of 38 nuclear families, each with three children affected with type 1 diabetes from the Human Biological Data Interchange. These were screened to identify potentially deleterious mutations. We then screened independent sets of 308 unrelated cases and 1003 controls to determine whether the identified mutations were more common in cases than controls. Finally we screened all 308 cases and 631 of the 1003 controls to determine whether rare polymorphisms, potential causal mutations, were more common in cases than controls. In order to select from the 38 initial families those that could potentially segregate a mutation among all affected members, each family was genotyped using 11 microsatellite markers spanning a 32 cM region surrounding the AGT locus on chromosome 1 (FIG. 1). This revealed that in 20 of the 38 families the affected individuals shared a haplotype in part of the 32 cM region.

The entire coding sequence, intron-exon boundaries, and 5' and 3' untranslated regions of AGT were screened for sequence variants in the genomic DNA of one affected member from each of the 20 nuclear families. Genomic DNA was amplified using primers positioned in introns flanking each exon of AGT (Table 1). Three families each contained a unique polymorphism in AGT, which we later determined segregated into all affected individuals in the family.

cleavage by renin (Inoue et al., 1997). It is also possible that mutation of Cys18 indirectly affects glycosylation of angiotensinogen. The partner with which Cys18 forms a disulfide bond, Cys138, lies in the middle of the N-glycosylation site Asn137-Cys138-Thr139 (FIG. 3b). Of the four N-glycosylation sites in angiotensinogen, Asn137 is the least glycosylated (Gimenez-Roqueplo et al., 1998b). In the absence of disulfide bond formation at Cys138, Asn137 might be glycosylated more frequently. Mutations in AGT that lead to increased glycosylation affect the amount of angiotensinogen secreted, and therefore indirectly the amount of Ang I (the peptide cleaved from AGT by renin and further converted to Ang II) produced (Gimenez-Roqueplo et al., 1996). Consequently, Cys18Arg would cause a decrease in Ang I formation.

Mutations detected in family 19 and family 30 were both in a 5' untranslated region of AGT. An alternative 5' exon of

TABLE 1

Primers Used in PCR Amplification for Mutation Detection

| Exon | PCR* | Forward primer (SEQ ID NO:) | Reverse primer (SEQ ID NO:) |
|---|---|---|---|
| alternative exon I | primary | 5'-CCTCGAAGTGGCCTATGGAA-3'(11) | 5'-GCGAGACTCTATGGGTGATG-3'(12) |
| | secondary | 5'-GACTGAGACTCTCCTGTTTC-3'(13) | 5'-CGGGGTGGCATCTTCAGTC-3'(14) |
| | secondary | 5'-TGGCACATTCTGCTCCTTAG-3'(15) | 5'-ATACAGCGAGTCCTGGTCT-3'(16) |
| | secondary | 5'-GACCAGGCAGTTGAGGAAGT-3'(17) | 5'-GATTCACACTCTCACGCTGC-3'(18) |
| promoter/5' genomic | primary | 5'-CCACTTTCCAGCATGTTACC-3'(19) | 5'-CTGCTATTCCTCCTGATGGC-3'(20) |
| | secondary | 5'-ACAGGCCCATGTGAGATATG-3'(21) | 5'-TGGTATTAGGGCACTGAAGG-3'(22) |
| | secondary | 5'-TGTGTTGAAGCAGGATCTTC-3'(23) | 5'-GATGCAGGCATTGAAAGATG-3'(24) |
| | secondary | 5'-GTGTTTAACAGTCTCCCCAGC-3'(25) | 5'-CTAGGTGTGTGACAGCCTGA-3'(26) |
| | secondary | 5'-CATGTCCCTGTGGCCTCTT-3'(27) | 5'-TGAGGGGTGGGGATGGAG-3'(28) |
| | secondary | 5'-CTGGTCATGTGAAACTTACC-3'(29) | 5'-ACCTTCAGCTGCTCCAAAGA-3'(30) |
| exon I | primary | 5'-CCACTTTCCAGCATGTTACC-3'(31) | 5'-CTGCTATTCCTCCTGATGGC-3'(32) |
| | secondary | 5'-AACCCTCCTCTCCAGCCT-3'(33) | 5'-TCATCACCGTGCCTCCTC-3'(34) |
| exon II | primary | 5'-TACTTGGACTTTGGGCTGAG-3'(35) | 5'-TTGAGCAAGGCACTTTGTTTC-3'(36) |
| | secondary | 5'-GGCTAAATGGTGACAGGGAAT-3'(37) | 5'-TAGGGCCTTTTCATCCACAG-3'(38) |
| | secondary | 5'-AATGCCGGGAAGCCAAAGA-3'(39) | 5'-TCCAAGGCTCCCAGATAGAG-3'(40) |
| | secondary | 5'-CTCTCCCCAACGGCTGTCTT-3'(41) | 5'-CTGCACAAACGGCTGCTTCA-3'(42) |
| | secondary | 5'-CTCTATCTGGGAGCCTTGGA-3'(43) | 5'-CACAGCCTGCATGAACCTGT-3'(44) |
| | secondary | 5'-TGAAGCAGCCGTTTGTGCAG-3'(45) | 5'-TCCCCACTTCTCAAGGGTG-3'(46) |
| | secondary | 5'-ACAGGTTCATGCAGGCTGTG-3'(47) | 5'-TCCCCACTTCTCAAGGGTG-3'(48) |
| exon III | primary | 5'-TGCCTCAGTGAACTCAAATGG-3'(49) | 5'-CTCCCCCTCCAAAACTACCA-3'(50) |
| | secondary | 5'-CAGGAGAATGCAGAGTGGC-3'(51) | 5'-GCAGGCGCTCTCAGTGAAG-3'(52) |
| | secondary | 5'-AGCACTGGAGTGACATCCAG-3'(53) | 5'-GATGGAGGACTGGTAGACAG-3'(54) |
| exon IV | primary | 5'-AAGGGGGAGGATGACTTAGT-3'(55) | 5'-GAAATTCCATCCAAATCCAG-3'(56) |
| | secondary | 5'-GTGCAAGGAGCATAAGCCTG-3'(57) | 5'-CTACTCTCCGCTCCCTCTT-3'(58) |
| exon V | primary | 5'-AAGGGGGAGGATGACTTAGT-3'(59) | 5'-GAAATTCCATCCAAAGTCCATG-3'(60) |
| | secondary | 5'-TAGCCCTCAGCACCCTG-3'(61) | 5'-TGTCCGGGGTTGTTATCTG-3'(62) |
| | secondary | 5'-AGAACACAGTGCCTGGCAAG-3'(63) | 5'-TTCACAAACAAGCTGGTCGG-3'(64) |
| | secondary | 5'-AGTGTTTAGCGCGGGACTAC-3'(65) | 5'-TTTGGAGGCTTATTGTGGCA-3'(66) |
| | secondary | 5'-TGAAAGATGCAAGCACCTGA-3'(67) | 5'-GAAAGCACTTTCGTTTGCAC-3'(68) |

*secondary primers had M13 forward and reverse universal sequences added to the 5' end.

Figure 3:
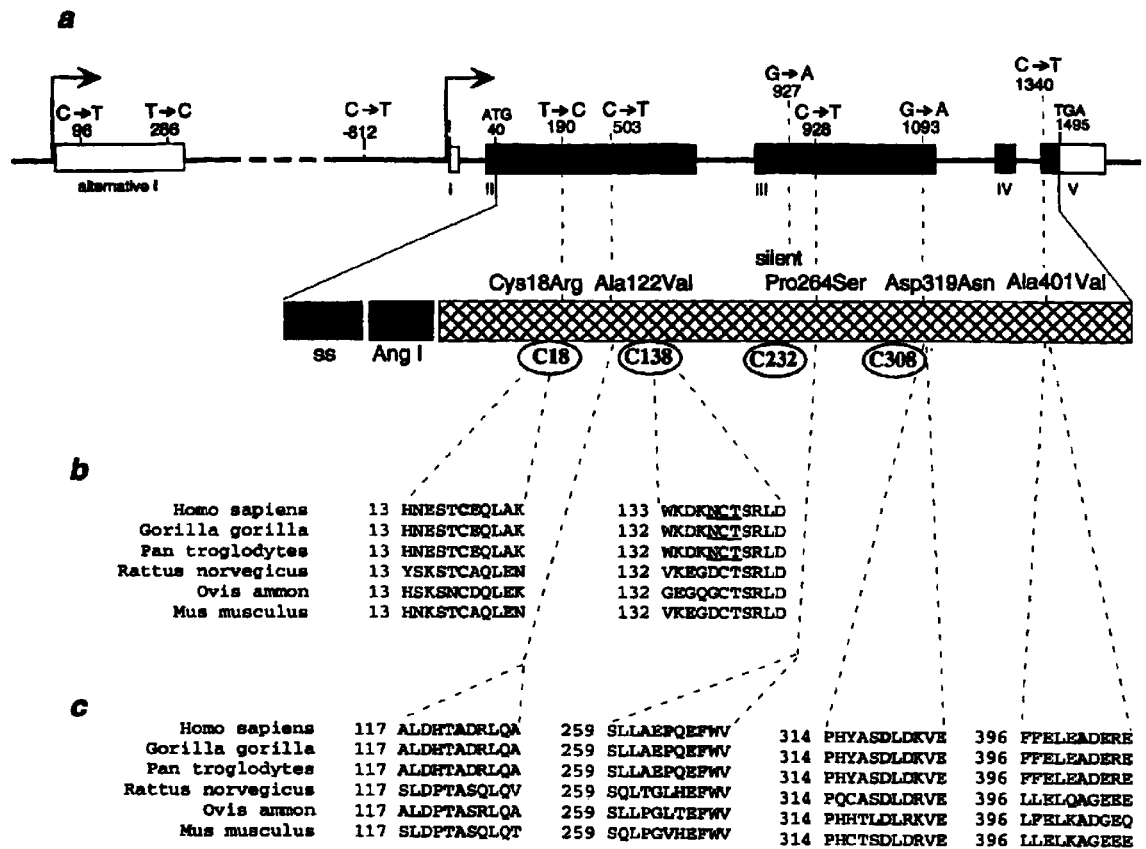

In family 24, a T to C transition was found in exon 2 at nucleotide 190 in the cDNA, which resulted in a substitution of arginine for cysteine at position 18 in the angiotensinogen mature peptide (FIG. 2a; FIG. 3a; 3b). Cys18 is one of two conserved cysteine residues in mammalian angiotensinogen (s) (FIG. 3) that has been shown in vitro to form a disulfide bond with Cys138 (Gimenez-Roqueplo et al., 1998a; Streatfeild-James et al., 1998). Disruption of disulfide bond formation might affect an unknown role for AGT in diabetes. Although it seems likely that disulfide bond formation contributes to a structurally constrained N-terminus (Streatfeild-James et al., 1998), disruption of the disulfide bond by in vitro mutagenesis of Cys18 did not affect the rate of angiotensinogen cleavage by renin (Gimenez-Roqueplo et al., 1998a). However, under physiological conditions, alteration of the protein's structure might disrupt association with other binding partners that would then indirectly affect AGT has been reported in the EST database. This alternate form was verified by PCR and sequencing in this study. We determined from our BAC contig that the alternative exon lies at least 100 kb upstream of the published exon I (FIG. 1, FIG. 3), and it was only detected by PCR in retina cDNA. The alternative exon that splices into exon II does not contain an open reading frame that extends out of the exon. Translation of the alternative transcript is predicted to begin at the first methionine in exon II (FIG. 3a) as previously reported (Gaillard et al., 1989). Although the alternative transcript produces the same angiotensinogen polypeptide as the published AGT cDNA, its expression could be regulated in a tissue-specific manner. It is not known what effect variants in the 5' untranslated region would have on the expression or stability of the transcript. A C to T transition at nucleotide 96 in the exon was seen in all affected individuals in family 19 (FIG. 2b; FIG. 3a). In family 30, a T to C transition at nucleotide 286 in this exon segregated with the disease (FIG. 2c; FIG. 3a).

Family 30 also contained a C to T transition at nucleotide 928 in exon 3, resulting in a on-conservative substitution of serine for proline at position 264 (FIG. 3a, 3c). This position is a proline in hominoids and a hydrophobic amino acid in other non-primate species (FIG. 3c); therefore the substitution of a hydrophilic amino acid (serine) is expected to have profound structural consequences. The Pro264Ser missense mutation is linked to a silent G to A transition at the preceding nucleotide, as well as to a C to T transition at −811 in the upstream genomnic sequence (shown in SEQ ID NO:1). This haplotype of three linked polymorphisms (C-811T, G927A and Pro264Ser) did not segregate into all the affected individuals in family 30 (FIG. 2d, 2e). However, this is not unexpected given that type 1 diabetes is a complex trait, and that predisposition to the disease probably involves a combination of mutations in multiple genes. If carrying a subset of these mutated genes results in the diabetic phenotype, members of the same family that do not share at the AGT locus could have an overlapping set of mutations in other gene(s).

Example 3

Identification of Additional Polymorphisms

If the AGT polymorphisms identified in Example B are truly predisposing mutations, they should be detected in other type 1 diabetic individuals and should be rare or absent in controls. To identify additional mutations, a set of DNA samples from 308 unrelated type 1 diabetic individuals was screened for sequence variants in AGT. These cases were selected from 308 additional families in the Human Biological Data Interchange. A set of control samples was screened in the same way for statistical comparison (see Example 1 and Table 2). The Cys18Arg mutation was observed three times in the new case set. It segregated with the disease in family 164, but not in families 214 and 344 (Table 2). The Cys18Arg mutation was observed in only 1 of 1003 control samples, indicating that it is enriched in the disease set (3 of 308 vs. 1 of 1003, p=0.03).

In the new case set the Pro264Ser mutation was seen once, with its accompanying polymorphisms, but was not seen in the controls (1/308 vs. 0/1003, p=0.09). The C-811T

TABLE 2

AGT Polymorphisms in Type 1 Diabetics

| Family ID | HBDI ID | Exon | Nucleotide change[a] | Change in AGT polypeptide | Segregation among affecteds | Observations in cases | Observations in controls[b] |
|---|---|---|---|---|---|---|---|
| 54 | B550 | alternative I[1] | G(26)T | 5' UTR | 1/2 | 1/328 | 0/639 |
| 19 | DCCT 20008 | alternative I | C(96)T | 5' UTR | 3/3 | 1/328 | 0/639 |
| 30 | CD2 2 | alternative I | T(286)C | 5' UTR | 3/3 | 1/328 | 0/639 |
| 30 | CD2 2 | 5' genomic[c,2] | C(−811)T[d] | — | 2/3 | 3/328 | 1/635 |
| 243 | A311 | " | " | — | 1/2 | " | " |
| 329 | CD328 | " | " | — | 2/2 | " | " |
| 114 | ENG8 | 5' genomic[c] | T(−741)C[e] | — | 2/2 | 1/328 | 0/635 |
| 114 | ENG8 | 5' genomic[c] | ΔG(−603)[e] | 2/2 | 1/328 | 0/635 | |
| 114 | ENG8 | 5' genomic[c] | C(−281)T[e] | — | 2/2 | 1/328 | 0/631 |
| 266 | DCCT 17123 | 5' genomic[c] | A(−715)G | 1/2 | 1/328 | 0/635 | |
| 162 | NM41 | 5' genomic[c] | T(−363)A | — | 1/2 | 1/328 | 0/633 |
| 339 | PM06 | 5' genomic[c] | G(−259)A | 2/2 | 1/328 | 0/631 | |
| 236 | A342 | 5' genomic[c] | T(−253)C | — | 2/2 | 1/328 | 0/631 |
| 150 | NM23A | 5' genomic[c] | G(−183)A | — | 2/2 | 1/328 | 0/631 |
| 24 | NM61 | II | T(190)C[3] | Cys18Arg[4] | 4/4 | 4/328 | 1/1003 |
| 164 | NM49 | " | " | " | 2/2 | " | " |
| 214 | C241 | " | " | " | 1/2 | " | " |
| 344 | DE3SAM3 | " | " | " | 1/2 | " | " |
| 305 | E428 | II | C(503)T | Ala122Val | 2/2 | 1/328 | 0/638 |
| 348 | NM42 | II | A(881)G | Tyr248Cys[f] | 1/2 | 1/328 | 2/638 |
| 30 | CD2 2 | III | G(927)A[d] | silent | 2/3 | 2/328 | 0/1003 |
| 243 | A311 | " | " | " | 1/2 | " | " |
| 30 | CD2 2 | III | C(928)T[d] | Pro264Ser | 2/3 | 2/328 | 0/1003 |
| 243 | A311 | " | " | " | 1/2 | " | " |
| 318 | PP 1 | III | G(1093)A | Asp319Asn | 1/2 | 1/328 | 0/628 |
| 119 | REQ380 | IV | C(1213)A[g] | Leu359Met | 1/2 | 1/328 | 0/635 |
| 272 | DCCT 19301 | V | C(1340)T | Ala401Val | 1/2 | 1/328 | 0/636 |
| 229 | NM68 | V | G(1529)T | 3' UTR | 3/3 | 1/328 | 1/636 |

[a]The number in parenthesis refers to the position of the nucleotide change relative to the start site of transcription, or the position in the alternative I exon as described in further detail herein.
[b]Total 639 controls were tested for each polymorphism, the number is <639 due to random sample failure. For the two recurrent mutations, additional control samples were tested.
[c]Refers to the genomic sequence upstream of the published exon I.
[d]The C(−811)T, G(927)A and C(928)T polymorphisms are linked in families 30 and 243.
[e]The T(−741), ΔG(−603) and C(−281)T polymorphisms are linked in family 114.
[f]This polymorphism was previously shown to affect the rate of angiotensinogen production in hypertensive individuals (Gimenez-Roqueplo et al., 1996).
[g]This polymorphism was reported previously in a hypertensive individual (Jeunemaitre, 1992).
[1]Position in alternative I refers to position within alternative exon I of SEQ ID NO:8, i.e. nucleotide 26 of alternative exon I is at position 176 of SEQ ID NO:8.
[2]Position in 5' genomic refers to position 5' of exon I of SEQ ID NO:1 where exon I starts at position 3012, i.e. nucleotide −811 of 5' genomic is at position 2201 of SEQ ID NO:1.
[3]Position with respect to exons II-V refer to nucleotide position in SEQ ID NO:6.
[4]Position with respect to amino acids refers to position in mature AGT peptide, i.e., the peptide of SEQ ID NO:8 having the signal peptide (residues 1–33) removed.

polymorphism was observed once in the controls but in isolation, not as part of the C-811T, G927A and Pro264Ser haplotype. The G297A change was not seen in the controls.

A number of novel polymorphisms in AGT were detected in the second set of unrelated diabetic individuals. Segregation analyses showed that about 50% of the polymorphisms segregated into all affected individuals within a family (Table 2). An individual in family 54 contained a G to T transversion at nucleotide 26 in alternative exon I. Within the genomic sequence upstream of exon I, the sequence variants A(-715)G, T(-363)A, G(-259)A, T(-253)C and G(-183)A were detected in individuals from families 266, 162, 339, 236 and 150, respectively. Three other polymorphisms in the upstream genomic sequence, T(-741)C, ΔG(-603) and C(-281)T, were linked in family 114. Although each of these changes lies upstream of the characterized proximal promoter in AGT (Brasier et al., 1999), they could potentially alter AGT expression by affecting promoter elements not yet identified. Recently, Yanai et al. (1999) have reported a role for hepatocyte nuclear factor 4 (HNF4) and chicken ovalabumin upstream pormoter transcription factor (COUP-TFII) in regulating transcription of the angiotensinogen gene. Truncating mutations in the HNF4 gene were found in patients with maturity onset diabetes of the youn, and the HNF4 gene is therefor also called MODY1 (Yamagata et al., 1996; Lidner et al., 1997). One of the DNA fragments identified as an HNF4 activating element by deletion analysis is the fragment from -242 to -295. Three of the variants in the sequence upstream of exon 1 are within this fragment (T(-253)C in family 236, G(-259)A in family 339 and C(-281)T in family 114). None of these variants was detected in 631 controls.

Three previously unreported missense mutations were detected in the coding sequence of AGT. An Ala122Val missense mutation was detected in family 305, an Asp319Asn was present in family 318, and an Ala401Val was found in family 272. Of these, only Ala122Val segregated with the disease in the family. Considering the rare missense mutations which were detected in AGT, five are at positions highly conserved in primates (Cys18Arg, Ala122Val, Pro264Ser, Asp319Asn, and Ala401Val, see FIG. 3b, 3c). In the 3' UTR a G to T transversion 35 bp downstream of the translation stop (G1530T) was observed in an individual from family 229. The discovery of enhancer elements in exon 5 and in the genomic sequence downstream of AGT (Nibu et al., 1994a; Nibu et al., 1994b) suggests this change might affect AGT expression. This change was detected once in 636 controls. Finally, two missense mutations that had been identified previously in hypertensive individuals were seen once in the set of type 1 diabetics. A Tyr248Cys mutation was detected in an individual from family 348. This change was previously reported to affect the rate of angiotensinogen production in hypertensive individuals (Gimenez-Roqueplo et al., 1996). An individual in family 119 contained a Leu359Met substitution that had been shown previously in a hypertensive patient (Jeunemaitre et al., 1992). Both changes were also found in our control samples (Table 2). Neither of these missense changes segregated with diabetes in these families.

All of the coding and nod-coding regions of AGT which were screened for polymorphisms in type 1 diabetics were also sequenced in 631 control individuals. Several polymorphisms were seen in the controls that were not seen in the cases (see Table 3). The frequency of rare changes, defined as present at less than 5 times in all samples, was compared in cases and controls. Fewer control samples carried rare changes when compared to type I diabetic cases (20 of 308 vs. 17 of 631, p=0.007). It is interesting to note that there were no polymorphisms detected in the sequence upstream of exon 1 between -64 and -413 in the 631 controls. There were five polymorphisms detected in this region in the type 1 diabetic cases including the three changes found in the fragment involved in activation of transcription of AGT by HNF4.

TABLE 3

AGT Rare Changes in Controls

| Control Sample # | Exon | Nucleotide change[a] | Corresponding change in AGT peptide | Amino Acid Conserved? | Observations in controls[b] | Observations in Type I cases |
|---|---|---|---|---|---|---|
| OS-93 | Alternative exon I | C(257)T[1] | 5' untranslated region | — | 1/639 | 0/328 |
| CA-158 | Alternative exon I | G(283)A | 5' untranslated region | — | 1/639 | 0/328 |
| CA-63 | Upstream genomic[c] | A(-854)T[2] | — | — | 1/635 | 0/328 |
| CA-103 | Upstream genomic[c] | C(-811)T | — | — | 1/635 | 3/328 |
| CEPH-57 | Upstream genomic[c] | C(-563)T | — | — | 1/633 | 0/328 |
| CEPH-67 | Upstream genomic[c] | C(-415)T | — | — | 1/633 | 0/328 |
| CA-153 | Upstream genomic[c] | C(-413)A | — | — | 1/633 | 0/328 |
| CA-172 | Upstream genomic[c] | C(-63)C | — | — | 1/631 | 0/328 |
| MY-37 | Exon II | T(190)C[3] | Cys(18)Arg[4] | Yes | 1/624 | 4/328 |
| CA-84 | Exon II | G(286)A | Ala(50)Thr | No, Thr in Rattus & Mus | 1/635 | 0/328 |
| CA-74 | Exon II | G(379)T | Gly(81)Cys | Yes | 1/635 | 0/328 |
| CA-199 | Exon II | C(748)T | Arg(204)Cys | Yes | 1/638 | 0/328 |
| AS-138 | Exon II | A(881)G | Tyr(248)Cys[d] | Yes | 2/638 | 1/328 |
| CA-197 | Exon II | A(881)G | Tyr(248)Cys[d] | Yes | 2/638 | 1/328 |
| CA-68 | Exon IV | C(1213)A | Leu(359)Met[e] | Yes | 1/635 | 1/328 |
| CA-139 | Exon IV | G(1246)A | Ala(370)Thr | No, Thr in all other species | 1/639 | 0/328 |
| AS-51 | Exon V | G(1469)A | Arg(444)His | No, Valine in ovis | 1/636 | 0/328 |

[a]The number in parenthesis refers to the position of the nucleotide change relative to the start site of transcription, or the position in the alternative I exon as further described herein.
[b]Total 639 controls were tested for each polymorphism, the number is <639 due to random sample failure.
[c]Refers to the genomic sequence upstream of the published exon I.
[d]This polymorphism was previously shown to affect the rate of angiotensinogen production in hypertensive individuals (Gimenez-Roqueplo et al., 1996).
[e]This polymorphism was reported previously in a hypertensive individual (Jeunemaitre et al., 1992).
[1]Position in alternative I refers to position within alternative exon I of SEQ ID NO:8, i.e. nucleotide 26 of alternative exon I is at position 176 of SEQ ID NO:8.

TABLE 3-continued

AGT Rare Changes in Controls

| Control Sample # | Exon | Nucleotide change[a] | Corresponding change in AGT peptide | Amino Acid Conserved? | Observations in controls[b] | Observations in Type I cases |
|---|---|---|---|---|---|---|

[2]Position in 5' genomic refers to position 5' of exon I of SEQ ID NO:1 where exon I starts at position 3012, i.e. nucleotide −811 of 5' genomic is at position 2201 of SEQ ID NO:1.
[3]Position with respect to exons II-V refer to nucleotide position in SEQ ID NO:6.
[4]Position with respect to amino acids refers to position in mature AGT peptide, i.e., the peptide of SEQ ID NO:8 having the signal peptide (residues 1–33) removed.

To conclude, the nature of the polymorphisms found in an initial set of diabetic families, their combined frequency in an independent set of cases compared with that in a set of controls (4/308 vs. 1/1003, p=0.008), and the abundance of rare mutations in type 1 diabetic cases all indicate that mutations in AGT increases susceptibility to the disease. The identification of missense mutations confirms the importance of the mature part of the protein in AGT structure and function. Novel polymorphisms in the alternative 5' exon could provide clues to tissue-specific functions of the renin-angiotensin system. The role of AGT in the microvascular complications of diabetes (Krolewski et al., 1998; Rogus et al., 1998) can be further considered. Perhaps the most interesting prospect is that our results in conjunction with the recent demonstration of angiotensin II receptors on cells of the islets of Langerhans that also stain for insulin, implies a direct role for AGT in pancreatic β-cell function (Tahmasebi et al., 1999). Understanding the contribution of AGT to type 1 diabetes could lead to new treatments and preventative medicines for the disease.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

List of References

Anand, R. (1992). *Techniques for the Analysis of Complex Genomes,* (Academic Press). Ausubel, F. M., et al. (1992). *Current Protocols in Molecular Biology,* (J. Wiley and Sons, NY).
Bartel, P. L., et al. (1993). "Using the 2-hybrid system to detect protein-protein interactions." In: *Cellular Interactions in Development: A Practical Approach,* Oxford University Press, pp. 153–179.
Bell, G. et al. (1984). Diabetes 33:176.
Borman S (1996). *Chemical & Engineering News,* December 9 issue, pp. 42–43.
Botstein, et al. (1980). *Am. J. Hum. Genet.* 32:314–331.
Capecchi, M. R. (1989). *Science* 244:1288.
Cariello (1988). *Human Genetics* 42:726.
Chee M, et al. (1996). *Science* 274:610–614.
Chevray, P. M. and Nathans, D. N. (1992). *Proc. Natl. Acad. Sci. USA* 89:5789–5793.
Conner, B. J., et al. (1983). *Proc. Natl. Acad. Sci. USA* 80:278–282.
Cornall, R. J. et al. (1991) *Nature* 353:262.
Cotton, et al. (1988). *Proc. Natl. Acad. Sci. USA* 85:4397–4401.
Davies, J. L. et al. (1994). *Nature* 371:130–136.
De Gouyon, B. et al. (1993). *Proc. Nat. Acad. Sci. USA* 90:1877.
DeRisi J, et al. (1996). *Nat. Genet.* 14:457–460.
Donehower, L. A., et al. (1992). *Nature* 356:215.
Erickson, J. et al., (1990). *Science* 249:527–533.
Feil et al., (1996). *Proc. Natl. Acad. Sci. USA* 93:10887–10890.
Fields, S. and Song, O-K. (1989). *Nature* 340:245–246.
Finkelstein, J., et al. (1990). *Genomics* 7:167–172.
Fodor, S. P. A. (1997). DNA Sequencing. Massively Parallel Genomics. *Science* 277:393–395.
Froguel, P. et al. (1992). *Nature* 356:162–164.
Froguel, P. et al. (1993). *N. Engl. J. Med.* 328:697–702.
Gagneten et al. (1997). *Nucl. Acids Res.* 25:3326–3331.
Garchon, H. J. et al. (1991). *Nature* 353:260.
Glover, D. (1985). *DNA Cloning,* I and II (Oxford Press).
Grompe, M., (1993). *Nature Genetics* 5:111–117.
Grompe, M., et al., (1989). *Proc. Natl. Acad. Sci. USA* 86:5855–5892.
Guthrie, G. and Fink, G. R. (1991). *Guide to Yeast Genetics and Molecular Biology* (Academic Press).
Hacia J G, et al. (1996). *Nature Genetics* 14:441–447.
Harlow and Lane (1988). *Antibodies: A Laboratory Manual* (Cold Spring Harbor Laboratory, Cold Spring Harbor, N.Y.
Harris, C. L. et al. (1996). *Nature Genet.* 13:161–166.
Harris, M. I. et al. (1987). *Diabetes* 36:523–534.
Harris, M. I., et al. (1992) *Diabetes Care* 15:815–819
Hasty, P., K., et al. (1991). *Nature* 350:243.
Hattersley, A. T. et al. (1992). *Lancet* 339:1307–1310.
Hodgson, J. (1991). *Bio/Technology* 9:19–21.
Hogan et al. (eds) (1994). *Manipulating the Mouse Embryo: A Laboratory Manual,* 2nd Edition, Cold Spring Harbor Laboratory Press, Cold Spring Harbor, N.Y.
Jablonski, E., et al. (1986). *Nuc. Acids Res.* 14:6115–6128.
Jakoby, W. B. and Pastan, I. H. (eds.) (1979). *Cell Culture. Methods in Enzymology,* Vol. 58 (Academic Press, Inc., Harcourt Brace Jovanovich (NY).
Jeffreys, et al. (1985). *Nature* 314:67–73.
Kadowaki et al. (1994). *N. Engl. J. Med.* 330:962–968.
King, H. and Zimmer, P. (1988). *Wld Hlth. Statist. Quart.* 41:190–196;
Kinszler, K. W., et al. (1991). *Science* 251:1366–1370.
Kinzler, K. W. and Vogelstein, B. 1997. *Nature* 386:761–763.
Kozlowski et al. (1993). *J. Recept. Res.* 13:1031–40.
Landegren, et al. (1988). *Science* 242:229.
Lee, J. E., et al. (1995). *Science* 268:836–844.
Lindner, T. et al. (1997). *J. Clin. Invest.* 100:1400–1405.
Lipshutz R J, et al. (1995). *BioTechniques* 19:442–447.
Litt, et al. (1989). *Am. J. Hum. Genet.* 44:397–401.
Lobe and Nagy (1998). *Bioessays* 20:200–208.
Lockhart D J, et al. (1996). *Nature Biotechnology* 14:1675–1680.
Mahtani, M. M. et al. (1996). *Nature Genetics* 14:90–94.
Maniatis. T., et al. (1982). *Molecular Cloning: A Laboratory Manual* (Cold Spring Harbor Laboratory, Cold Spring Harbor, N.Y.).

Matthews and Kricka (1988). *Anal. Biochem.* 169:1.
Mittlin (1989). *Clinical Chem.* 35:1819.
Modrich, P. (1991). *Ann. Rev. Genet.* 25:229–253.
Mombaerts, P., et al (1992). *Cell* 68:869.
Morahan, G. et al. (1994). *Proc. Nat. Acad. Sci. USA* 91:5998
Nakamura, et al. (1987). *Science* 235:1616–1622.
Newton, C. R., et al. (1989). *Nucl. Acids Res.* 17:2503–2516.
Nguyen, Q., et al. (1992). *BioTechniques* 13:116–123.
Novack, et al. (1986). *Proc. Natl. Acad. Sci. USA* 83:586.
Orita, et al. (1989). *Proc. Natl. Acad. Sci. USA* 86:2776–2770.
Osterrieder and Wolf (1998). *Rev. Sci. Tech.* 17:351–364.
Philpott, K. L., et al. (1992). *Science* 256:1448.
Prochazka, M. et al. (1987). *Science* 237:286.
Rano and Kidd (1989). *Nucl. Acids Res.* 17:8392.
Rigby, P. W. J., et al. (1977). *J. Mol. Biol.* 113:237–251.
Rosa et al (1998). *FEBS Letters* 436:267–270.
Rotter et al. (1990). *Diabetes Mellitus: Theory and Practice*, 378–413.
Samanen et al. (1991). *J. Med. Chem.* 34:3036–43.
Sambrook, J., et al. (1989). *Molecular Cloning: A Laboratory Manual*, 2$^{nd}$ Ed. (Cold Spring Harbor Laboratory, Cold Spring Harbor, N.Y.).
Serreze, D. et al. (1994). *J. Exp. Med.* 180:1553.
Shastry et al. (1995). *Experientia* 51:1028–1039.
Shastry et al. (1998). *Mol. Cell. Biochem.* 181:163–179.
Sheffield, V. C., et al. (1989). *Proc. Natl. Acad Sci. USA* 86:232–236.
Sheffield, V. C., et al. (1991). *Am. J. Hum. Genet.* 49:699–706.
Shenk, et al. (1975). *Proc. Natl. Acad. Sci. USA* 72:989.
Shinkai, Y., et al. (1992). *Cell* 68:855.
Shoemaker D D, et al. (1996). *Nature Genetics* 14:450–456.
Skolnick, M. H. and Wallace, B. R. (1988). *Genomics* 2:273–279.
Snouwaert, J. N., et al. (1992). *Science* 257:1083.
Steiner et al. (1990). *Diabetes Care* 13:600–609.
Tavtigian, S., et al. (1996). *Nature Genetics* 12:333–337.
Taylor et al. (1992). *Endocrine Rev.* 13:566–595.
Todd, J. A. (1990). *Immunol. Today* 11:122.
Todd, J. A., et al. (1991). *Nature* 351:542.
Van den Ouwenland, J. M. W. et al. (1992). *Nature Genet.* 1:368–371.
Verge, C. F. et al. (1998). *J. Clin. Invest.* 102:1569–1575.
Wartell, R. M., et al. (1990). *Nucl. Acids Res.* 18:2699–2705.
Weber and May (1989). *Am. J. Hum. Genet.* 44:388–396.
Wells, J. A. (1991). *Methods in Enzymol.* 202:390–411.
White, M. B., et al., (1992). *Genomics* 12:301–306.
White and Lalouel (1988). *Ann. Rev. Genet.* 22:259–279.
Yamagata, K. et al. (1996). *Nature* 384:458–460.
Yanai, K. et al. (1999). *J. Biol. Chem.* 274:34605–34612.

List of Patents and Patent Applications:

U.S. Pat. No. 4,376,110.
U.S. Pat. No. 4,486,530.
U.S. Pat. No. 4,868,105.
U.S. Pat. No. 4,873,191.
U.S. Pat. No. 5,093,246.
U.S. Pat. No. 5,550,050.
U.S. Pat. No. 5,800,998.
U.S. Pat. No. 5,837,492.
U.S. Pat. No. 5,891,628.
EPO Publication No. 225,807
EP 425,731A.
European Patent Application Publication No. 0332435
Geysen, H., PCT published application WO 84/03564, published 13 Sep. 1984
WO 90/07936.
WO 92/19195.
WO 93/07282
WO 94/25503.
WO 95/01203.
WO 95/05452.
WO 96/02286.
WO 96/02646.
WO 96/11698.
WO 96/40871.
WO 96/40959.
WO 97/12635.

What is claimed is:

1. An isolated nucleic acid selected from the group consisting of:
a DNA molecule comprising the nucleotide sequence set forth in SEQ ID NO:8 and the complement thereof.

2. A method for detecting an alteration in angiotensinogen wherein said alteration is associated with insulin-dependent diabetes mellitus in a human subject, wherein said method comprises analyzing an angiotensinogen gene or an angiotensinogen gene expression product from the human subject for a polymorphism in the angiotensinogen gene and associating the polymorphism with insulin-dependent diabetes mellitus wherein said polymorphism is in the nucleic acid of claim 1.

3. The method of claim 2 wherein the sequence of the angiotensinogen gene is compared with the sequence of one or more wild-type angiotensinogen gene sequences.

4. A method for determining whether a human subject has or is at risk for developing diabetes mellitus comprising the steps of:
a) obtaining a sample from the human subject, the sample comprising the nucleic acid of claim 1 of the angiotensinogen gene; and
b) detecting the presence or absence of a genetic polymorphism associated with insulin-dependent diabetes mellitus in the angiotensinogen gene of the subject, wherein the presence of said genetic polymorphism identifies a subject that has or is at risk for developing diabetes.

5. An isolated nucleic acid selected from the group consisting of:
(a) a DNA molecule comprising the nucleotide sequence set forth in SEQ ID NO:8 or the complement thereof, wherein G at nucleotide position 26 is substituted with T;
(b) a DNA molecule comprising the nucleotide sequence set forth in SEQ ID NO:8 or the complement thereof, wherein C at nucleotide position 96 sequence is substituted with T; and
(c) a DNA molecule comprising the nucleotide sequence set forth in SEQ ID NO:8 or the complement thereof, wherein T at nucleotide position 286 is substituted with C.

6. A method for determining whether a human subject has or is at risk for developing diabetes mellitus comprising the steps of:
a) obtaining a sample from the subject, the sample comprising nucleic acid containing the angiotensinogen gene; and b) detecting the presence or absence of a genetic polymorphism in the angiotensinogen gene of the subject, wherein the presence of the genetic polymorphism identifies a subject that has or is at risk for developing diabetes, and
wherein the polymorphism is selected from the nucleic acids of claim 5.

7. The method of claim 2 wherein the polymorphism of the angiotensinogen gene is selected from the nucleic acids of claim 5.

* * * * *